(12) United States Patent
Biscup et al.

(10) Patent No.: US 7,824,444 B2
(45) Date of Patent: Nov. 2, 2010

(54) EXPANDABLE SPHERICAL SPINAL IMPLANT

(75) Inventors: Robert S. Biscup, Chagrin Falls, OH (US); Clayton G. Leroux, Avon, OH (US)

(73) Assignee: Spineco, Inc., Avon, OH (US)

( * ) Notice: Subject to any disclaimer, the term of this patent is extended or adjusted under 35 U.S.C. 154(b) by 1082 days.

(21) Appl. No.: 10/801,975

(22) Filed: Mar. 16, 2004

(65) Prior Publication Data

US 2004/0186576 A1  Sep. 23, 2004

Related U.S. Application Data

(60) Provisional application No. 60/455,875, filed on Mar. 20, 2003.

(51) Int. Cl.
*A61F 2/44* (2006.01)
(52) U.S. Cl. .................................................. 623/17.12
(58) Field of Classification Search ... 623/17.11–17.16, 623/4.1, 6.11, 6.56, 6.59, 6.64
See application file for complete search history.

(56) References Cited

U.S. PATENT DOCUMENTS

| | | | |
|---|---|---|---|
| 4,349,921 A | 9/1982 | Kuntz | |
| 4,714,469 A | 12/1987 | Kenna | |
| 4,834,757 A | 5/1989 | Brantigan | |
| 4,878,915 A | 11/1989 | Brantigan | |
| 4,936,848 A | 6/1990 | Bagby | |
| 4,961,740 A | 10/1990 | Ray et al. | |
| 5,059,193 A | 10/1991 | Kuslich | |
| 5,123,926 A | 6/1992 | Pisharodi | |
| 5,192,327 A | 3/1993 | Brantigan | |
| 5,258,031 A | 11/1993 | Salib et al. | |
| 5,306,307 A | 4/1994 | Senter et al. | |
| 5,306,308 A | 4/1994 | Gross | |
| 5,425,772 A | 6/1995 | Brantigan | |
| 5,425,773 A | 6/1995 | Boyd et al. | |
| 5,562,738 A | 10/1996 | Boyd et al. | |
| 5,571,189 A | 11/1996 | Kuslich | |
| 5,607,424 A | 3/1997 | Tropiano | |
| 5,609,635 A | 3/1997 | Michelson | |
| 5,645,596 A | 7/1997 | Kim et al. | |
| 5,658,337 A | 8/1997 | Kohrs et al. | |
| 5,674,296 A | 10/1997 | Bryan et al. | |
| 5,720,751 A | 2/1998 | Jackson | |
| 5,743,918 A | 4/1998 | Calandruccio et al. | |

(Continued)

FOREIGN PATENT DOCUMENTS

FR  2 797 179  2/2001

(Continued)

OTHER PUBLICATIONS

Fernstrom Intervertebral Disc Arthroplasty: A Long-Term Evaluation, Alvin H. McKenzie, MD, MChOrth, FRCS ©.

(Continued)

*Primary Examiner*—Anu Ramana
(74) *Attorney, Agent, or Firm*—Fay Sharp LLP; Brian E. Turung

(57) ABSTRACT

A prosthetic implant for forming a support structure between adjoining vertebrae in a spinal column. The prosthetic implant includes a generally spherical or ellipsoidal body that at least partially engages a surface of adjacent vertebrae.

55 Claims, 8 Drawing Sheets

U.S. PATENT DOCUMENTS

| | | | |
|---|---|---|---|
| 5,766,252 A | 6/1998 | Henry et al. | |
| 5,782,832 A | 7/1998 | Larsen et al. | |
| 5,782,919 A | 7/1998 | Zdeblick et al. | |
| 5,824,093 A | 10/1998 | Ray et al. | |
| 5,876,456 A | 3/1999 | Sederholm | |
| 5,888,224 A | 3/1999 | Beckers et al. | |
| 5,888,226 A | 3/1999 | Rogozinski | |
| 5,888,227 A | 3/1999 | Cottle | |
| 5,895,428 A | 4/1999 | Berry | |
| 6,019,792 A | 2/2000 | Cauthen | |
| 6,042,380 A * | 3/2000 | De Rowe | 433/173 |
| 6,059,829 A | 5/2000 | Schlapfer et al. | |
| 6,080,158 A | 6/2000 | Lin | |
| 6,093,207 A | 7/2000 | Pisharodi | |
| 6,113,638 A | 9/2000 | Williams et al. | |
| 6,179,874 B1 | 1/2001 | Cauthen | |
| 6,214,050 B1 | 4/2001 | Huene | |
| 6,245,108 B1 | 6/2001 | Biscup | |
| 6,264,695 B1 | 7/2001 | Stoy | |
| 6,383,519 B1 | 5/2002 | Sapieszko et al. | |
| 6,478,822 B1 | 11/2002 | Leroux et al. | |
| 6,533,818 B1 | 3/2003 | Weber | |
| 2001/0032020 A1 | 10/2001 | Besselink | |

FOREIGN PATENT DOCUMENTS

| | | |
|---|---|---|
| WO | WO 00/13619 | 3/2000 |
| WO | WO 00/42953 | 7/2000 |
| WO | WO 00/44319 | 8/2000 |
| WO | WO 02/085262 | 10/2002 |

OTHER PUBLICATIONS

Arthroplasty with Intercorporal Endoprothesis in Herniated Disc and in Painful Disc, Ulf Fernstrom.

* cited by examiner

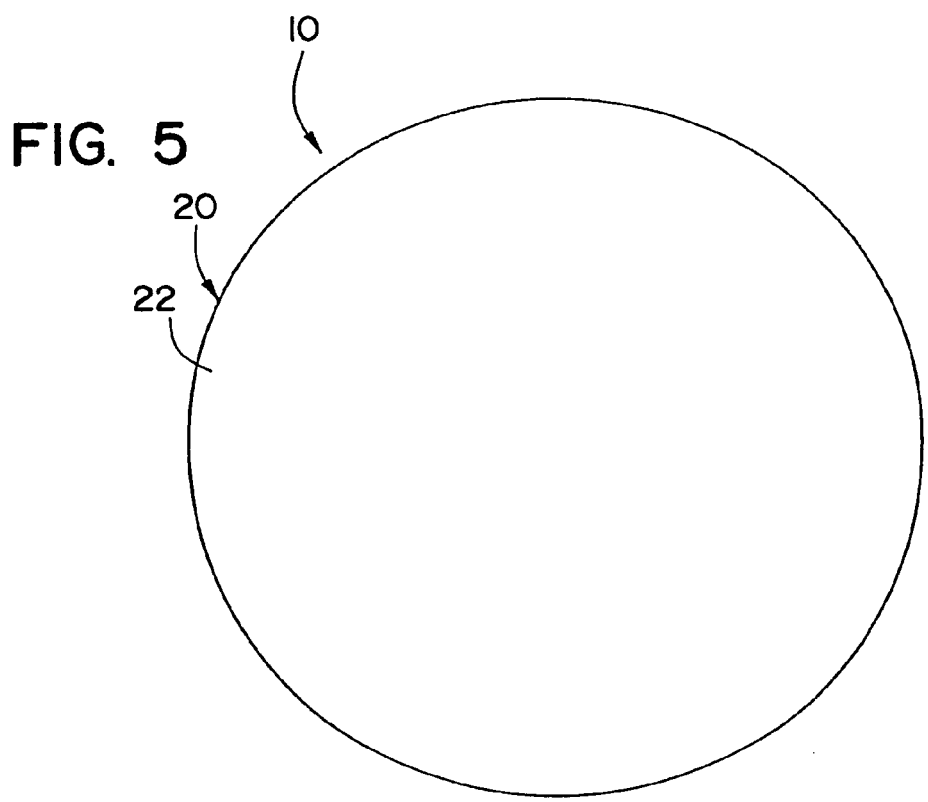
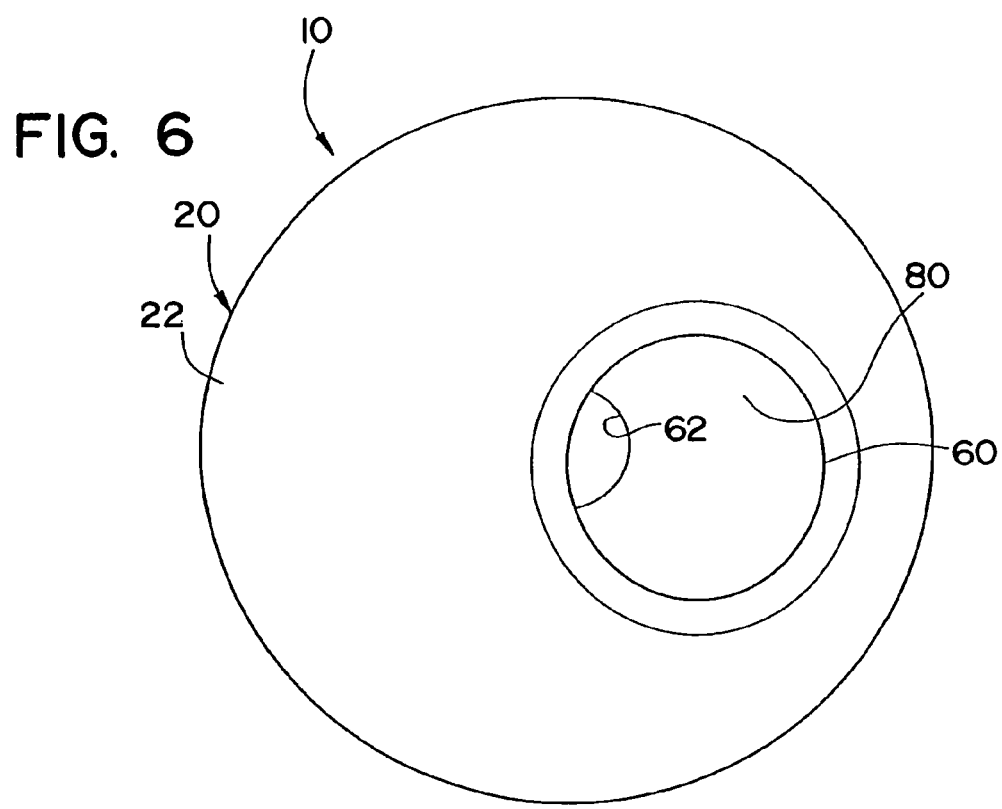

EXPANDABLE SPHERICAL SPINAL IMPLANT

This application claims priority on U.S. Provisional Application Ser. No. 60/455,875, filed Mar. 20, 2003 entitled "Banded Spherical Spinal Implant."

The present invention pertains to prosthetic implants, and more particularly to interbody spinal prosthetic implants to fuse two or more vertebrae together, and even more particularly to interbody spinal prosthetic implants that provide a substitute for an intervertebral disc and/or that provides a spacer between two vertebrae.

INCORPORATION BY REFERENCE

U.S. Provisional Application Ser. No. 60/455,875, filed Mar. 20, 2003, entitled "Banded Spherical Spinal Implant" is incorporated by reference. Also incorporated herein by reference is U.S. Pat. No. 6,478,822 entitled "Spherical Spinal Implant."

BACKGROUND OF THE INVENTION

The human spine is made up of a column of more than thirty bones and their adjoining structures. The vertebrae near the head are known as the presaccral vertebrae which are separate bones capable of individual movement. The bodies of these vertebrae are connected by anterior and posterior ligaments and by discs of fibrocartilage generally known as intervertebral discs. These discs are positioned between opposite faces of adjacent vertebral bodies. This column of vertebrae and intervertebral discs form a central axis that supports the head and torso. These vertebrae also enclose an opening through which the spinal cord passes.

The presaccral vertebrae are normally held in position to one another by the intervertebral discs, ligaments and musculature of the body. These vertebrae move relative to adjacent vertebrae thus permitting the head to be turned relative the body, and provide a wide range of flexibility to the spine.

One of the most costly health problems involves back pain and the pathology of the spine. Such problems can affect individuals of all ages and can result in significant suffering to such individuals. Back pain can be caused by several factors. Some of these factors include congenital deformities, traumatic injuries, degenerative changes to the spine, etc. Congenital deformities, traumatic injuries or degenerative changes to the spine can result in painful excessive motion, collapse of a motion segment resulting in the contraction of the spinal canal and compressing the neural structures causing debilitating pain, paralysis or other problems, which in turn can result in nerve root compression or spinal stenosis.

Nerve conduction disorders can also be associated with intervertebral discs or the vertebrae themselves. One such condition is herniation of the intervertebral disc, in which a small amount of tissue protrudes from the sides of the disc into the foramen to compress the spinal cord. A second common condition involves the development of small bone spurs, termed osteophytes, along the posterior surface of the vertebral body, again impinging on the spinal cord.

Upon identification of these conditions, surgery may be required to correct the problem. For those problems associated with the formation of osteophytes or herniations of the intervertebral disc, one such surgical procedure is intervertebral discectomy. In this procedure, the involved vertebrae are exposed and the intervertebral disc is removed, thus removing the offending tissue or providing access for the removal of the bone osteophytes. A second procedure, termed a spinal fusion, may then be required to fix the vertebrae together to prevent movement and maintain a space originally occupied by the intervertebral disc. Although this procedure may result in some minor loss of flexibility in the spine, the minor loss of mobility is typically acceptable due to the relatively large number of vertebrae.

During a spinal fusion following a discectomy, a prosthetic implant for the spinal is inserted into the intervertebral space. This prosthetic implant is often a bone graft removed from another portion of the patient's body, termed an autograph. The use of bone taken from the patient's body has the important advantage of avoiding rejection of the prosthetic implant, but has several shortcomings. There is always a risk in opening a second surgical site to obtain the implant. For instance, opening a second surgical site can lead to infection or pain for the patient, and/or the site may be weakened by the removal of bony material which could result in other injuries. The bone used to form the prosthetic implant may not be perfectly shaped and/or placed, leading to slippage or absorption of the implant, and/or failure of the bone implant to fuse with the vertebrae.

Other options for a graft source of material for the prosthetic implant are bone removed from cadavers, termed allograft, or from other species, termed a xenograft. In these cases, while there is the benefit of not having a second surgical site opened, there are increased problems associated with graft rejection and the risk of transmitting communicable diseases.

An alternative approach to using bone from the patient or other sources to form the prosthetic implant is to make the prosthetic implant from a synthetic material that is biologically compatible with the body and the vertebrae. Several compositions and geometries of such prosthetic implants have been utilized with varying success. These prosthetic implants have had shapes ranging from simple blocks of material to carefully shaped prosthetic implants.

There have been an extensive number of attempts to develop an acceptable prosthetic implant that can be used to replace an intervertebral disc and yet maintain the stability of the intervertebral disc spaced between adjacent vertebrae, at least until complete arthrodesis is achieved. These prosthetic implants have taken many forms. While many types of synthetic prosthetic devices have been proposed, the success ratio has been low and the surgical procedures have been complicated and often traumatic to the patient. Some of these prosthetic implants are designed to be pounded into the intervertebral disc space and the vertebral end plates. Other prosthetic implants have been developed that do not have a constant cross-section or are in the form of a sphere.

The various prosthetic implants that have been developed can be generally divided into two basic categories, namely solid implants and implants designed to encourage bone ingrowth. Prosthetic implants which promote natural bone ingrowth achieve a more rapid and stable arthrodesis. These prosthetic implants are typically filled with autologous bone prior to insertion into the intervertebral disc space. These prosthetic implants typically include apertures which communicate with openings in the prosthetic implant, thereby providing a path for tissue growth between the vertebral end plate and the bone or bone substitute within the prosthetic implant. When a prosthetic implant is selected to be fused with the vertebrae, the intervertebral disc space for a prosthetic implant is typically prepared by reducing the end plates of the vertebrae to bleeding bone so as to facilitate tissue growth with the prosthetic implant.

A number of difficulties still remain with the many prosthetic implants currently available. While it is recognized that hollow implants which permit bone ingrowth in the bone or bone substitute within the prosthetic implant are an optimum technique for achieving fusion, most of these devices have difficulty achieving the desired amount of fusion, at least without the aid of some additional stabilization systems (e.g., cage, rod, screw, nail, post, plate, etc.). Moreover, some of the prosthetic implants are not structurally strong enough to support the heavy loads applied at the most frequently fused vertebral levels, mainly those in the lower lumbar spine.

In view of the present state of technology related to prosthetic implants, there is a continued need for new prosthetic implant designs that optimize the bone ingrowth capabilities, when desired, are strong enough to support the vertebrae until arthrodesis occurs, can maintain or restore normal spinal anatomy at the instrumented segment, and/or exhibit reduced slippage when inserted between vertebrae, thereby diminishing the occurrence of nerve pinching.

SUMMARY OF THE INVENTION

The present invention pertains to an improved implant, and more particularly to an improved prosthetic implant for insertion between one or more vertebrae and a method for inserting the prosthetic implant between one or more vertebrae.

In accordance with one aspect of the present invention, a prosthetic implant is used to at least partially support adjoining vertebrae in a spinal column. The prosthetic implant includes a substantially spherical or ellipsoidal body and at least one expandable component. The at least one expandable component can be part of the substantially spherical or ellipsoidal body and/or a separate component from the substantially spherical or ellipsoidal body. The at least one expandable component can be used to at least partially form at least one stabilizer. The at least one stabilizer can be expanded into a substantial disc shape or some other shape. The at least one expandable component can include at least one biologically active substance. The at least one biologically active substance can be coated on the at least one expandable component and/or contained in the at least one expandable component. At least a portion of the at least one expandable component can include a substantially smooth surface or non-smooth surface. The expanded radial width of the at least one expandable component can be substantially constant or variable. The expanded thickness of the at least one expandable component can be substantially constant or variable. The at least one expandable component can expand radially outwardly from the substantially spherical or ellipsoidal body at an angle that is along or deviates from a substantially constant axis. The at least one expandable component can include at least one tapered edge in an expanded state. The at least one expandable component and said substantially spherical or ellipsoidal body can be formed of the same or different materials. The substantially spherical or ellipsoidal body can include one portion of a plurality of portions. When the substantially spherical or ellipsoidal body includes a plurality of portions, each portion can have the same or different shape, size, structure, composition, etc. The at least one expandable component can include an elastic material at least prior to the at least one expandable component being expanded. The elastic material can be formed of and/or be included in an expandable pouch. The material that at least partially forms the expandable material can be at least partially hardenable. The substantially spherical or ellipsoidal body can include a mechanical compression arrangement that is adapted to at least partially compress together at least two portions of said spherical or ellipsoidal body. The substantially spherical or ellipsoidal body can include a memory material. The substantially spherical or ellipsoidal body can include at least one electrical connection. The substantially spherical or ellipsoidal body can include at least one pressure sensor.

In accordance with another and/or alternative aspect of the present invention, the prosthetic implant includes a body that is designed and constructed in a generally spherical or ellipsoidal (e.g., ovoid, etc.) shape manufactured either as a single piece or as a multi-piece structure. The prosthetic implant is primarily designed for insertion between two vertebrae; however; it will be appreciated that the concepts associated with the prosthetic implant can be used in other regions of the body. The prosthetic implant is designed to at least partially emulate the space between two vertebrae. The prosthetic implant is designed to provide improved spinal support fixation and methodology which provides stability between adjacent vertebrae and in which the shape will facilitate in securing the prosthetic implant between the vertebrae. The prosthetic implant can be designed to be easily and efficiently positioned between two vertebrae and to facilitate in the reduction of the failure rate of prosthetic implants between the vertebrae. The prosthetic implant can include one or more surfaces that reduce pinching with the spinal cord and other body parts closely adjacent to the prosthetic implant. The prosthetic implant can include two hemispherical shaped pieces with a common central reduced core around which a shapeable module of material is capable of expanding into various shapes (e.g., tourus shaped, donut shaped, etc.) by one or more mechanisms. The prosthetic implant can include two hemispherical shapes that are connected to central component which is expandable to form a stabilizer. The expandable middle portion of the prosthetic implant (e.g., a tourus, a cylindrical component, etc.) can be designed to be expandable in a lateral manner at an angle (perpendicular, 0.01-89.90°, 90.01-179.99°, etc.) to the surface of the sphere-construct or in a manner that will create a circumferential edge to the expanded component. The expansion of the middle portion can be accomplished by one or more mechanisms such as, but not limited to, intentional triggering of the expansion by electro-stimulation and/or chemical reaction, expansion by the use of hydraulic pressure (e.g., injecting a fluid into the middle portion and/or another portion of the prosthetic implant to induce the expansion, activating a pump on and/or in the prosthetic implant to include the expansion, etc.), use of a memory metal and/or polymer to induce the expansion, using the force applied on the prosthetic device by the vertebrae to induce expansion, clamping one or more ends of the prosthetic implant to induce expansion, rotating a screw or positioning a mechanical component on and/or in the prosthetic implant to induce expansion, activating a motor on/or in the prosthetic implant to induce expansion, etc. The middle portion can be designed to expand a set amount or a variable amount. The middle portion can be designed to be expandable from the outer surface of the spherical or oval body of the prosthetic implant a length of about 0.01%-300% the diameter of the spherical or oval body so as to permit the surgeon to select the most appropriate configuration for insertion into disc space based upon the size and location of the affected vertebra. The angle of articulation of the expanded middle portion in relation to the surface of the sphere or oval body can be varied from an angle of at least about 0.01° to an angle of up to about 180°. The middle portion can be designed to uniformly expand beyond its lateral border or be designed so that one or more sections of the middle portion expand while one or more other sections remain in their original locus or expand at a different amount. The middle portion can also be designed so that the angle of expansion is uniform or designed so that one or more sections have an angle of expansion that is different from one or more other sections. The middle portion can also be designed so that the thickness and/or profile of the expanded middle portion is uniform or designed so that one or more sections have thickness and/or profile that is different from one or more other sections. The prosthetic implant can include one or more threaded interior cavities which can be used to receive a threaded rod to facilitate in the insertion of the prosthetic implant between the vertebrae. A threaded "plug" or cap can be used to at least partially close or seal the threaded opening during and/or after the prosthetic implant has been properly placed between two vertebrae. The prosthetic implant can be designed to receive one or more bone-growth substances and/or medicines to be at least partially packed into one or more cavities and/or channels of the prosthetic implant. The packing of the one or more cavities and/or channels can occur prior to, during and/or after the insertion of the prosthetic implant between the vertebrae. Alternatively, or in additionally, the packing of the one or more cavities and/or channels can occur post-surgically (e.g., endoscopic surgery, etc.). A "plug" or cap can be used to at least partially cover or seal one or more cavities or channels after the packing has been inserted. The one or more plugs are also used to inhibit or prevent the growth/extensis of bone into one or more cavities and/or openings so as to reduce or inhibit thin threads of bone growth from entering the one or more cavities or channels, which thin threads of bone growth are prone to breakage and potential formation of jagged edges or floating bone particles. The prosthetic implant can include a tracer marker which can be visible on radiographic film, on MRI imagery, on ultrasound detection and/or other types of sound wave detection, by some other electromagnetic detection, etc. The tracer maker can be located on and/or within the prosthetic implant so as to provide the surgeon with a method of monitoring the implant's location and/or movement. Various prosthetic implants can be constructed with various sizes of radii of the body and/or stabilizer so as to allow a properly sized prosthetic implant to be selected for insertion between two particular spinal vertebrae. The prosthetic implant can be coated on the exterior with one or more materials to facilitate and/or enhance bone growth, inhibit rejection of the prosthetic implant, promote healing in and/or about the prosthetic implant, and/or to deliver medicine and/or other biological active substances about the prosthetic implant. Some of the coating materials can include, but are not limited to, (i) a polymer-based or other bone cement; (ii) expanded polymer or urethane foam; (iii) epoxy; (iv) autologous growth compound, powdered bone or another compound of an appropriate biologic agent(s) and/or (v) pharmaceuticals to diminish pain and/or stimulate bone growth. The prosthetic implant can be designed to have a smoothly polished exterior. The prosthetic implant can be designed to have one or more regions of the exterior pitted, matte and/or otherwise formed of a roughened or non-smooth exterior, including the cutting of grooves or channels in the exterior. The prosthetic implant can include one or more non-smooth surfaces to help secure the prosthetic implant in position between the vertebrae. The prosthetic implant can have one or more channels or cavities filled prior to, during and/or after insertion of the prosthetic implant; and/or one or more portions of the prosthetic implant can be coated on the exterior so as to permit and/or facilitate the introduction of medicine for pain relief, to promote healing, to inhibit rejection, to enhance flexibility, to enhance rigidity and/or for one or more other beneficial purposes. The prosthetic implant can include materials that are bioabsorbable or non-bioabsorbable. When the prosthetic implant includes bioabsorbable materials, the bioabsorbable materials can become resorbed so that, over a predetermined period of time, the mechanism or designated portions thereof will be resorbed by the body. The prosthetic implant can be at least partially coated with a bioactive material to stimulate bone growth and/or to enhance fixation of the anchor into the bone. The prosthetic implant can be at least partially coated with a bioresistive material to deter bone growth and/or to resist fixation of the spinal implant into the bone. A special set of tooling can be designed for use with the prosthetic implant to facilitate the insertion of the spinal implant. The prosthetic implant is typically designed such that one prosthetic will be utilized and inserted into the space between two vertebrae created by the removal of all or a portion of a spinal disc in the spinal column to provide support to the vertebrae that is repaired or the spinal disc partially or wholly removed during the surgical process. Prior to, after and/or during insertion of the prosthetic implant, the prosthetic implant will have the middle portion expanded so as to enhance or create a stabilizer on the prosthetic implant, which stabilizer facilitates in the healing process. Typically, the prosthetic implant is inserted in a location to avoid intrusion into the spinal cord area while at the same time avoiding migration or extending outside the vertebral column. The prosthetic implant can be formed or include a variety of materials such as, but not limited to, sterilized and shaped bone (human and/or mammalian), polymer material, a biocompatible carbon fiber, materials that simulate and/or are the equivalent of bone, reinforced polymers, traditional orthopedic implant materials (e.g., titanium, chrome cobalt, stainless steel, etc.), and/or a resorbable material. The prosthetic implant can be at least partially made of a material which closely approximates the elasticity of the vertebrae and/or the intervertebral disc.

BRIEF DESCRIPTION OF THE DRAWINGS

The invention may take physical form in certain parts and arrangement of parts, preferred embodiments of which will be described in detail and illustrated in the accompanying drawings which form a part hereof and wherein:

FIG. 5 is an enlarged perspective view of still another modified prosthetic implant of the present invention;

FIG. 6 is an enlarged perspective view of yet another modified prosthetic implant of the present invention;

DESCRIPTION OF THE PREFERRED EMBODIMENTS

Figure 1:
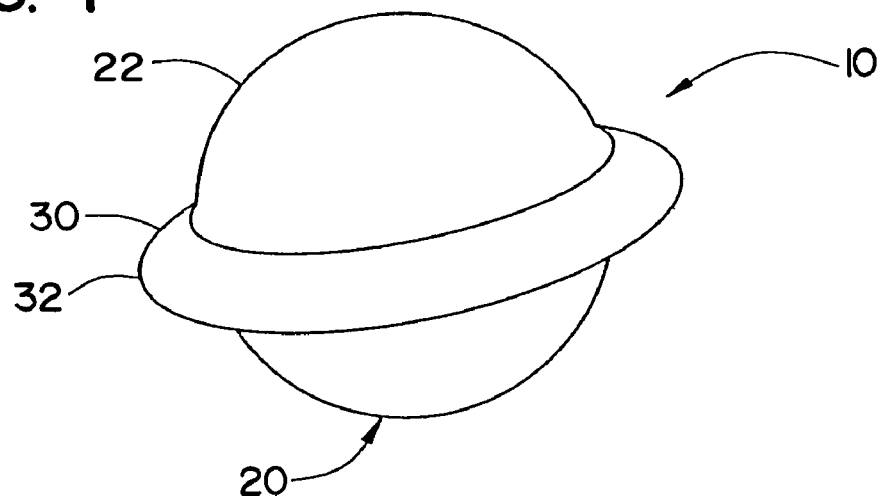
FIG. 1 is an enlarged perspective view of the prosthetic implant of the present invention.

Referring to the drawings, wherein the showings are for the purpose of illustrating a preferred embodiment of the invention only and not for the purpose of limiting same, FIG. 1 illustrates a prosthetic device or implant 10 which is designed to be inserted in an intervertebral disc space between two vertebrae of the spinal column. Prosthetic implant 10 is illustrated as having a spherical body 20 that has an outer surface 22. As can be appreciated, body 20 can have other shapes. Spherical body 20 can be made of a variety of materials such as, but not limited to, bone, stainless steel, titanium, chromemolybdenum, cobalt chromium alloy, ceramic (zirconium oxide ceramic, aluminum oxide ceramic, etc.), chrome or chrome alloys, cobalt or cobalt alloys, polycarbonate, polypropylene, polyethylene, polymethylmethacrylate, polysolfone types filled with glass and/or carbon fibers, and various types of carbon and fiber reinforced polymers. The particular material or materials selected will generally depend on the location of the implant and the various objectives to be accomplished by the implant. Spherical body 20 can include one or more biologically active substances and/or biologically neutral substances (e.g., medicine, bone and/or tissue growth promoters, bone and/or tissue growth inhibitors, cement, etc.) that are mixed with or form the materials of spherical body 20. One or more of the biologically active substances and/or biologically neutral substances can be used to flow or otherwise escape from spherical body 20 and enter the bone, tissue and/or fluids about the prosthetic implant, and/or interact with the bone, tissue and/or fluids about the prosthetic implant, and/or one or more of the biologically active substances and/or biologically neutral substances can be retained on and/or in the spherical body.

The prosthetic implant is formed of a biologically compatible material for use in humans; however, the prosthetic implant can be formed of one or more materials that are compatible with other vertebrates (e.g., dog, cat, horse, etc.). The prosthetic implant is shaped and sized for at least partial insertion between two vertebrae. The prosthetic implant is designed to be at least partially placed in the intervertebral disc space that was formerly occupied by at least a portion of an intervertebral disc. The intervertebral disc is partially or completely removed prior to insertion of the prosthetic implant between the vertebrae. The prosthetic implant is designed to be readily inserted by established surgical procedures, and/or designed to reduce or minimize chances of surgical difficulty. The geometry of the prosthetic implant is selected to facilitate in better obtaining and/or desired load bearing and/or support through the vertebrae so as to reduce and/or minimize the likelihood of the prosthetic implant dislocating relative to the vertebrae during surgery and/or during the post operative procedure. The prosthetic implant is capable of achieving arthrodesis (fusion) and/or arthroplasty (joint formation) between adjacent vertebrae, depending on the desired procedure. As such, the prosthetic implant allows the surgeon to cause either a multidirectional joint or a fusion to form between two of more vertebrae. The prosthetic implant is at least partially designed to reduce or eliminate nerve pressure caused by a damaged or removed disc.

Referring now to FIG. 1, prosthetic implant 10 includes a spherical body 20 that has an outer surface 22 which is illustrated as substantially smooth; however, it will be appreciated that the body can have other shapes and/or the outer surface can include one or more non-smooth surfaces. The maximum radius or radii of the generally spherical or ellipsoidal body can be varied depending upon the location of the prosthetic implant between particular vertebrae. Typically, the maximum radius or radii of the generally spherical or ellipsoidal body for adult human use will vary from about 2-20 mm; however, another radius or radii can be used. The maximum radius or radii of the generally spherical or ellipsoidal body is selected so that the generally spherical or ellipsoidal body can be at least partially positioned between the two adjacently positioned vertebrae and the surrounding fibers and muscles that complete the spinal structure. The maximum radius or radii of the generally spherical or ellipsoidal body can be selected to cause two adjacently positioned vertebrae to at least partially separate from one another a distance greater than their relative positions prior to surgery. The spreading of the adjacently positioned vertebrae from their original positions results in the elastic nature of the surrounding tissue and muscles at least partially maintaining the inserted prosthetic implant in compression between the vertebrae. The maximum radius or radii of the generally spherical or ellipsoidal body can alternatively be selected to cause two adjacently positioned vertebrae to at least partially separate from one another a distance generally equal to or less than their relative positions prior to surgery. The maximum radius or radii of the generally spherical or ellipsoidal body is typically selected so that the generally spherical or ellipsoidal body is fully positional within the perimeter of the intervertebral disc space when properly positioned between two vertebrae.

The prosthetic implant is made of a material that is inert and/or biologically compatible with the vertebrae and/or surrounding tissue about the vertebrae. The material of the prosthetic implant can include, but is not limited to, bone; stainless steel; titanium; chromemolybdenum; cobalt chromium alloy; ceramic (zirconium oxide ceramic, aluminum oxide ceramic, etc.); chrome or chrome alloys; cobalt or cobalt alloys; polycarbonate; polypropylene; polyethylene; polymethylmethacrylate; polysolfone types filled with glass and/or carbon fibers; and/or various types of carbon and fiber reinforced polymers. As can be appreciated other and/or alternate materials can be used. The one or more materials used can be wear resistant, have an increased frictional coefficient, and/or have a reduced frictional coefficient. The selected material for used in adult humans is designed to maintain a tension load of at least about five pounds on the disc tissue and/or vertebral endplate, and typically about ten to forty pounds on the disc tissue and/or vertebral endplate; however, the prosthetic implant can be designed to maintain other tension loads. The selected tension load facilitates in maintaining the prosthetic implant in position between the vertebrae. When the prosthetic implant is used in a nonhuman, the tension load design for the prosthetic implant can be selected accordingly. At least a portion of the material used to form the prosthetic implant can have an elasticity which approximates the elasticity of the vertebrae. The prosthetic implant can beat least partially coated with, made up of, and/or contain a tracer marker which facilitates in the location of the prosthetic implant in a body, the location of a particular portion or region of the prosthetic implant in a body, and/or positioning of the prosthetic implant during and/or after a surgical procedure. The tracer marker can include a material that is visible on radiographic film (e.g., X-ray), on MRI imagery and/or other magnetic wave imagery, on ultrasound detection and/or other types of sound wave detection, and/or by some other electromagnetic detection (e.g., microwaves, infrared waves, radio waves, ultraviolet waves, etc.). The prosthetic implant can include one or more pressure sensors to determine the amount of pressure being applied to the prosthetic implant and/or at one or more regions on the prosthetic implant. The one or more pressure sensors can be located on the surface and/or inside the prosthetic implant. The one or more pressure sensors can include one or more visual indicators to display information about the pressure being applied, and/or the one or more pressure sensors can include a storage device, transmitter, etc. that can be used to transmit and/or store information about the pressure being applied on the prosthetic implant.

The interior of spherical body 20 can be solid, hollow or have one or more cavities. If spherical body 20 includes one or more cavities, the cavities can be empty or at least partially filled with one or more biologically active substances and/or biologically neutral substances that can alter the physical characteristics of spherical body 20 (i.e., weight distribution, density distribution, etc.) and/or which can flow or otherwise escape the void and enter the bone, tissue and/or fluids about the implant. Prosthetic implant 10 also includes a stabilizer 30 on spherical body 20. Stabilizer 30 is illustrated as disc shaped and extending about the central axis of spherical body 20; however, it will be appreciated that the stabilizer can have other shapes and/or be positioned in other locations on body 20. The stabilizer can be made of or include materials that are the same or similar to the material(s) of spherical body 20; however, the stabilizer can include different or additional materials. As can be appreciated, stabilizer 30 can be a separate component that is later connected and/or formed on outer surface 22.

Stabilizer 30 is designed to facilitate in at least partially orienting the prosthetic implant between one or more vertebrae, limiting the amount of movement of the generally spherical or ellipsoidal body between one or more vertebrae, and/or facilitating in the insertion of the prosthetic implant between one or more vertebrae. Edge 32 of stabilizer 30 typically is a rounded, non-sharp edge; however, this is not required. The rounding off of the surfaces of the stabilizer reduces and/or eliminates pinching of the nerve leading from the spinal cord which can result in pain, damage and/or paralysis to the individual. Stabilizer 30 is illustrated as having a thickness that reduces as the distance increases from spherical body 20; however, the thickness can be designed to remain generally constant, increase in thickness, increase and then decrease, decrease and then increase, etc. Stabilizer 30 has a maximum thickness that is less than the diameter of spherical body 20. Generally, the maximum thickness of the stabilizer is less than about 1.5 times the diameter of spherical body 20, and can be less than about four (4) times the diameter of spherical body 20; however, other thicknesses can be used. Stabilizer 30 is shown to have a generally constant width that radially extends outwardly from spherical body 20; however, the width of the stabilizer can vary. Generally, the maximum radial width of the stabilizer is less than about two (2) times the diameter of spherical body 20, and typically less than about one (1) times the diameter of spherical body 20; however, other radial widths can be used.

Figure 2:
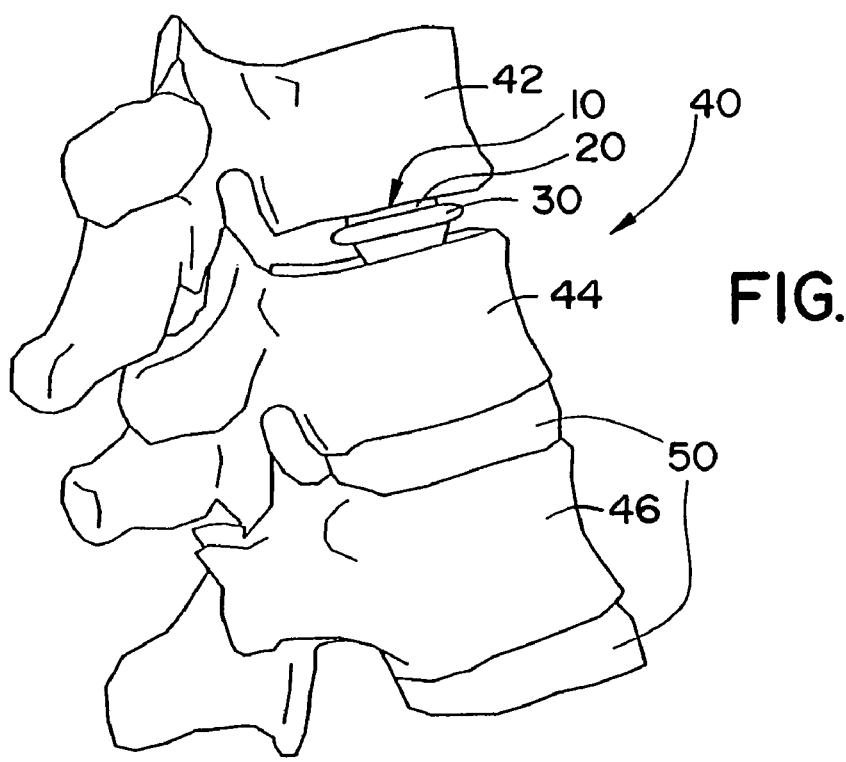
FIG. 2 is an enlarged side elevation view of a portion of a spinal column which includes the prosthetic implant of the present invention positioned between two adjacently positioned vertebrae.

Referring now to FIG. 2, prosthetic implant 10 is shown as inserted into a human vertebra column 40. Human vertebra column 40 includes several vertebrae 42, 44, 46 and includes intervertebral disc 50 positioned between two adjacently positioned vertebrae. Prosthetic implant 10 is designed to partially or fully replace a damaged intervertebral disc. As shown in FIG. 2, vertebrae 42 and 44 are separated by, and at least partially supported on, spherical body 20 of prosthetic implant 10. The remaining vertebrae are illustrated as supported on, and separated by, intervertebral disc 50 which maintains a space between the adjoining vertebrae. The damaged portions of intervertebral disc 50 have been at least partially removed from the region between vertebrae 42 and 44 prior to prosthetic implant 10 being inserted therebetween. The inner surfaces of vertebrae 42 and 44 are also prepared prior to prosthetic implant 10 being inserted therebetween. Such preparation typically includes cleaning the region between the vertebrae of unwanted materials, removing bone and/or tissue from the surface of one or more vertebrae, inserting separators between the vertebrae, and/or the like. After the region between the vertebrae has been prepared, prosthetic implant 10 is at least partially inserted into the space between the vertebrae. Depending of the design of prosthetic implant 10, the prosthetic implant will achieve arthrodesis (fusion) and/or arthroplasty (joint formation) between adjacent vertebrae. Once prosthetic implant 10 has been inserted between vertebrae 42 and 44, stabilizer 30 limits the movement of prosthetic implant 10 between the vertebrae.

Figure 3:
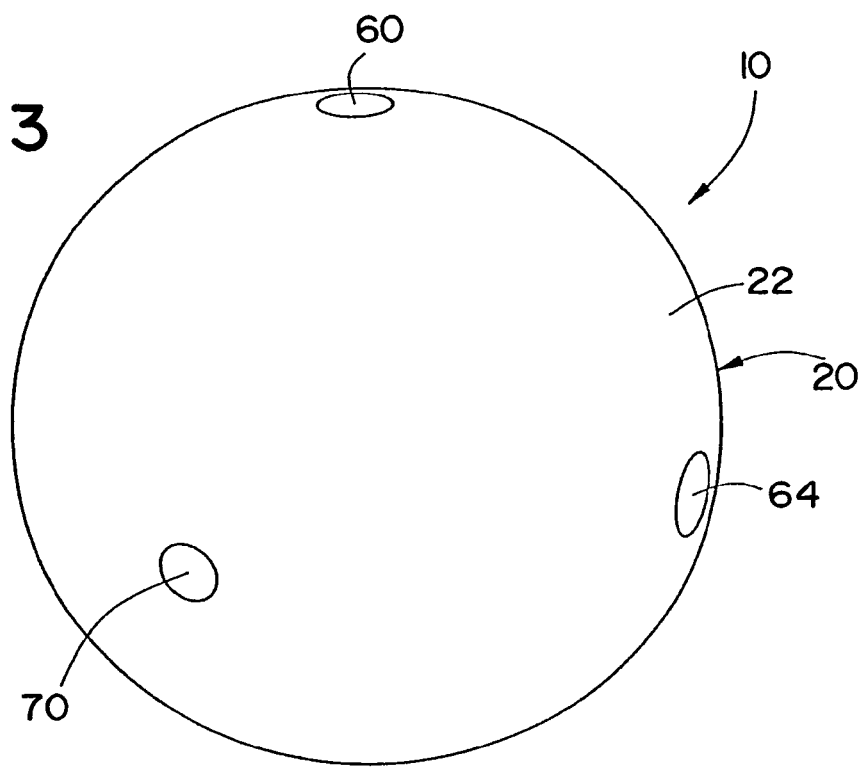
FIG. 3 is an enlarged perspective view of a modified prosthetic implant of the present invention.

Referring now to FIGS. 3-8, several other configurations of the prosthetic implant are illustrated. In each of these configurations, the stabilizer is not shown so that the features of body 20 can be better illustrated. Consequently, it will be appreciated that the various configurations of body 20 shown in FIGS. 3-8 are usable in conjunction with one or more stabilizers. Referring specifically to FIG. 3, spherical body 20 includes several openings 60, 64 and 70. The openings are illustrated as circular shaped; however, other shapes can be used. The size of the openings is selected so that various biologically active substances and/or biologically inactive substances can be packed therein and/or to enable bone and/or tissue to grow in one or more of the openings. When biologically active substances and/or biologically inactive substances are packed into the openings, the packed material typically includes, but is not limited to, medicine, tissue, cells, and the like. It will be appreciated that the stabilizer can also or alternatively include one or more openings so that various biologically active substances and/or biologically inactive substances can be packed therein, enable bone and/or tissue to grow in one or more of the openings, and/or to allow fluids to flow therethrough. One or more of the openings can also be used to enable an instrument to be connected to the implant to facilitate in the insertion and/or positioning of the implant between the vertebrae. The instrument can be used to insert the prosthetic implant in the intervertebral disc space in a number of different approaches such as from an anterior, posterior, lateral, and/or lateralscopic approach to the vertebrae. The opening for the instrument is typically threaded to receive a threaded instrument; however, other types of connections can be used between the instrument and the body. The threaded opening allows an instrument to be simply secured to and/or removed from the prosthetic implant 10. One or more of the openings can also or alternatively be used to secure pedicle screws to the prosthetic implant to facilitate in the attachment of a rod or plate of a stabilization system to the prosthetic implant.

Figure 4:
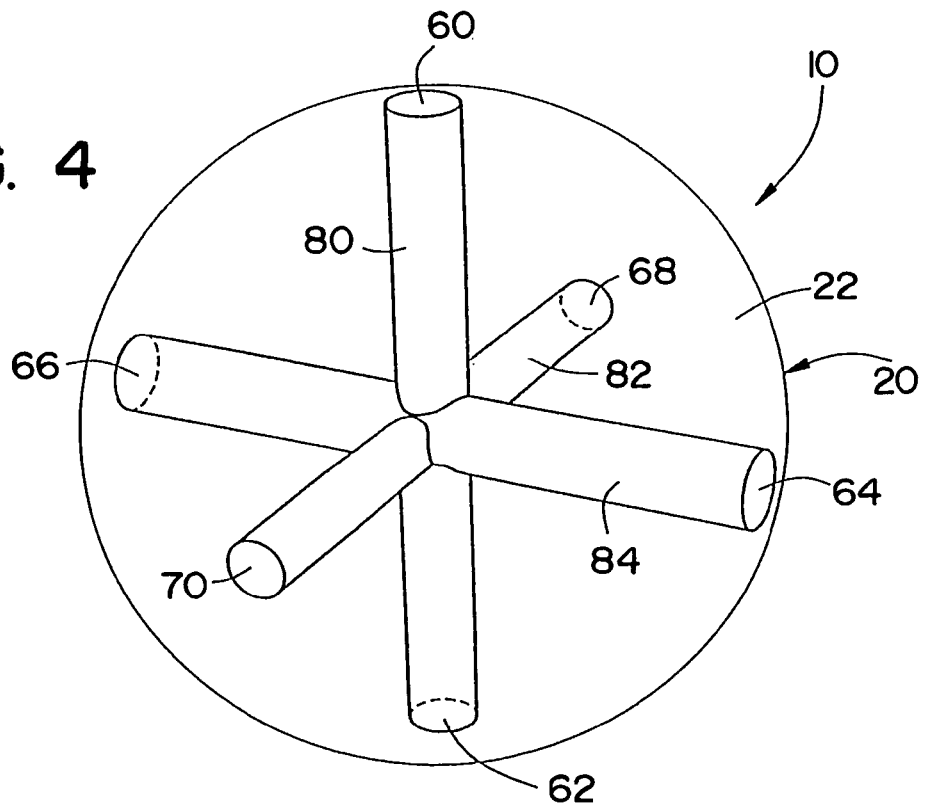
FIG. 4 is an enlarged perspective view of another modified prosthetic implant of the present invention.

Referring now to FIG. 4, prosthetic implant 10 includes a spherical body 20 that has a plurality of cavities 80, 82 and 84. The cavities have a substantially cylindrical shape and extend through implant 10; however, other shapes can be used. The cavities are illustrated as all passing straight through the center of spherical body 20; however, it can be appreciated that one or more of the cavities do not pass through the center of spherical body 20 and/or one or more of the cavities can be non-straight. Cavity 80 includes openings 60 and 62, cavity 82 includes openings 68 and 70 and cavity 84 includes openings 64 and 66. The cavities typically include biologically active substances and/or biologically inactive substances, and/or enable bone and/or tissue to grow into one or more of the openings and cavities; however, the cavities can be empty to allow fluids to flow therethrough or remain vacant. It will be appreciated that the stabilizer can also or alternatively include one or more cavities so that various biologically active substances and/or biologically inactive substances can be packed therein, enable bone and/or tissue to grow into one or more of the openings and cavities, and/or allow fluids to flow therethrough. One or more of the openings can also or alternatively be used to enable an instrument to be connected to the implant to facilitate in the insertion and/or positioning of the implant between the vertebrae, and/or connect to one or more components of a stabilization system. The remaining portion of the interior of spherical body 20 can be solid, hollow or have one or more cavities. If spherical body 20 includes one or more cavities, the cavities can be empty or at least partially filled with biologically active substances and/or biologically inactive substances which alter the physical characteristics of spherical body 20 (i.e., weight distribution, density distribution, etc.) and/or which are designed to flow or otherwise escape the cavity and enter the bone, tissue and/or fluids about the prosthetic implant.

Referring now to FIG. 5, prosthetic implant 10 includes a spherical body 20 that has no openings. The interior of spherical body 20 can be solid, hollow or have one or more cavities. If spherical body 20 includes one or more cavities, the cavities can be empty or at least partially filled with biologically active substances and/or biologically inactive substances which alter the physical characteristics of spherical body 20 (i.e., weight distribution, density distribution, etc.) and/or which is designed to flow or otherwise escape the cavity and enter the bone, tissue and/or fluids about the prosthetic implant. It will be appreciated that the stabilizer can also or alternatively have no openings.

Referring now to FIG. 6, prosthetic implant 10 includes a spherical body 20 that has two openings 60 and 62 and a cylindrical cavity 80 extending therebetween. The cavity typically includes biologically active substances and/or biologically inactive substances packed therein; however, the cavities can be empty to allow fluids to flow therethrough. The single cavity is illustrated as having a volume that is greater than the individual volumes of cavities 80, 82 and 84 of FIG. 4. The remaining portion of the interior of spherical body 20 can be solid, hollow or have one or more cavities. If spherical body 20 includes one or more of these other cavities, the cavities can be empty or at least partially filled with biologically active substances and/or biologically inactive substances which alter the physical characteristics of spherical body 20 (i.e., weight distribution, density distribution, etc.) and/or which is designed to flow or otherwise escape the cavity and enter the bone, tissue and/or fluids about the prosthetic implant.

Figure 7:
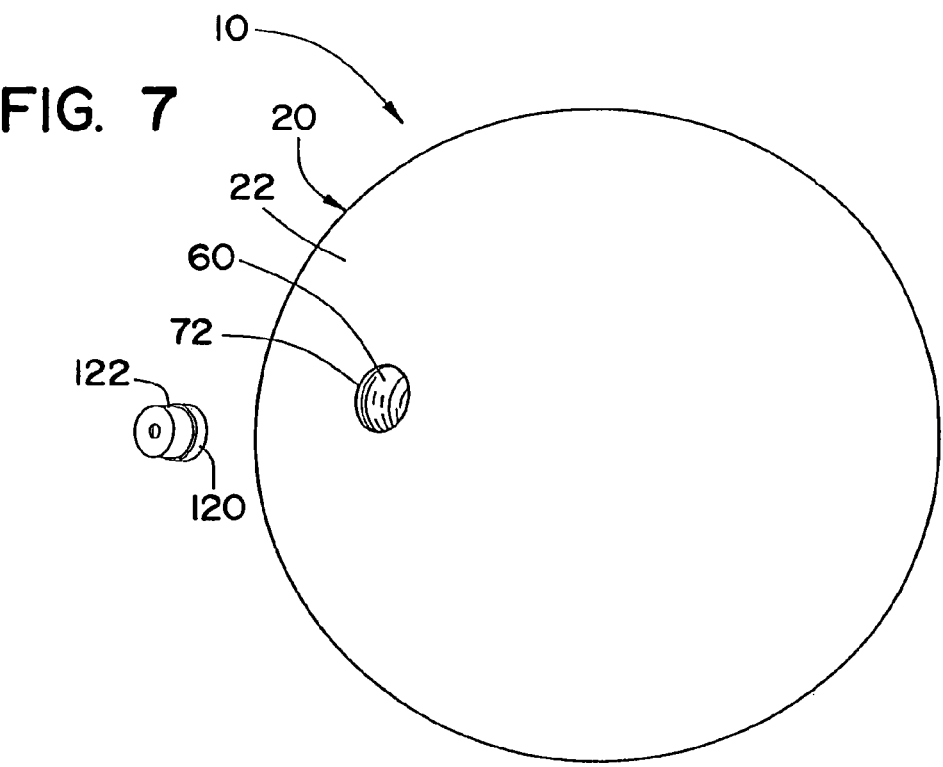
FIG. 7 is an enlarged perspective view of still yet another modified prosthetic implant of the present invention.

Referring now to FIG. 7, prosthetic implant 10 includes a spherical body 20 that has opening 60 that includes a threaded interior 72 designed to receive an insertion instrument, a pedicle screw and/or a cap 120. Cap 120 includes threading 122 that threads into opening 60 to at least partially close opening 60. Cap 120 can be designed to partially or fully seal opening 60. The cap can be designed to be removable or nonremovable. The cap can be designed to enable one or more biologically active substances and/or biologically inactive substances pass through the cap, and/or inhibit or prevent one or more biologically active substances and/or biologically inactive substances from passing through the cap. The cap can be designed to enable one or more biologically active substances and/or biologically inactive substances to be removed from and/or refilled into opening 60. Such removal and/or refilling can be accomplished by the removal of the cap, by designing a cap that enables a needle or syringe to pass therethrough, and/or by including one or more openings in the cap. The cap can be designed to additionally or alternatively function as a pressure sensor. The cap itself could be a pressure sensor or contain a pressure sensor. The information obtained from the pressure sensor can be used to determine the prosthetic implant conditions and/or status of the prosthetic implant. As can be appreciated, the pressure information can be used for other and/or additional purposes.

Figure 8:
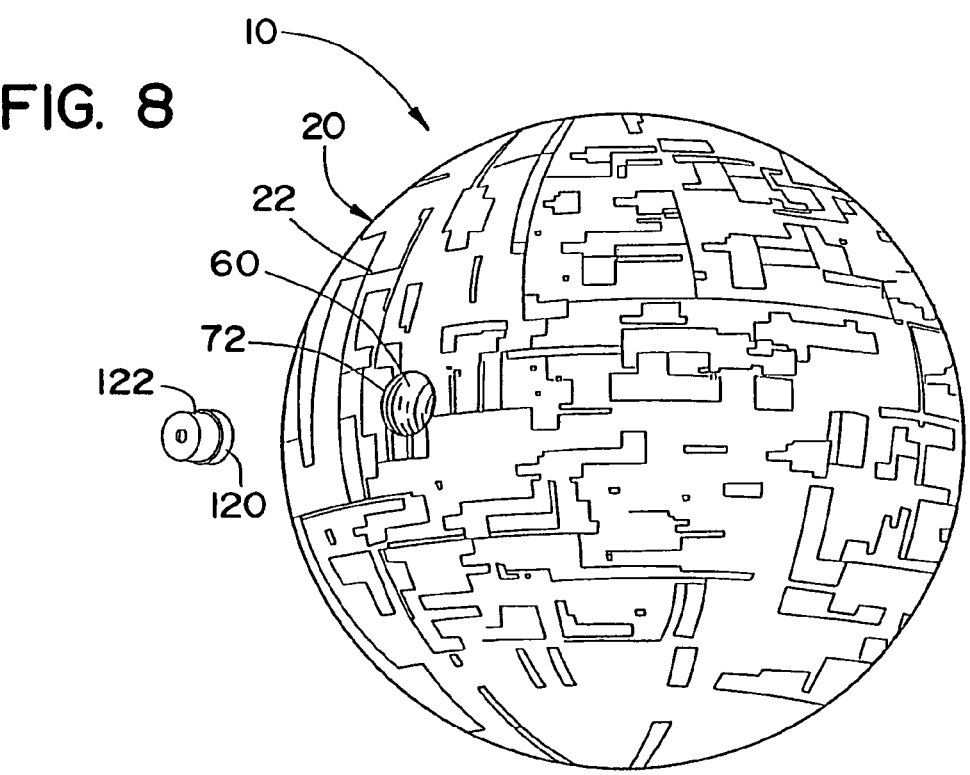
FIG. 8 is an enlarged perspective view of a further modified prosthetic implant of the present invention.

Referring now to FIG. 8, prosthetic implant 10 is similar to the prosthetic implant shown in FIG. 7 and illustrates an outer surface 22 that is non-smooth. The non-smooth surface can be used to facilitate in the surface of the implant becoming partially or fully fused with one or more vertebrae. The non-smooth surface can also be designed to engage with and/or anchor to the underside surface of vertebrae within the intervertebral disc space. It will be appreciated that the stabilizer can also or alternatively include a non-smooth surface.

Figure 9:
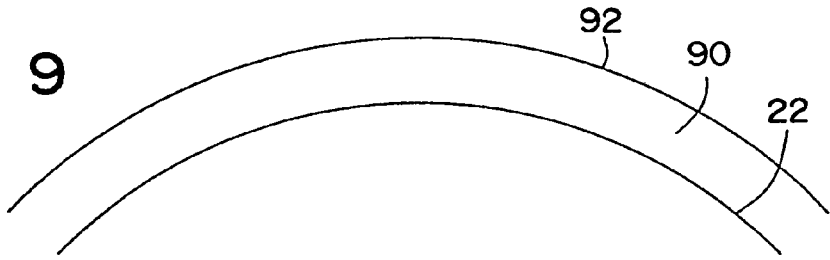
FIG. 9 is an enlarged sectional view of the surface of the prosthetic implant illustrating a coating material applied to a smooth outer surface of the body of the prosthetic implant.
Figure 10:
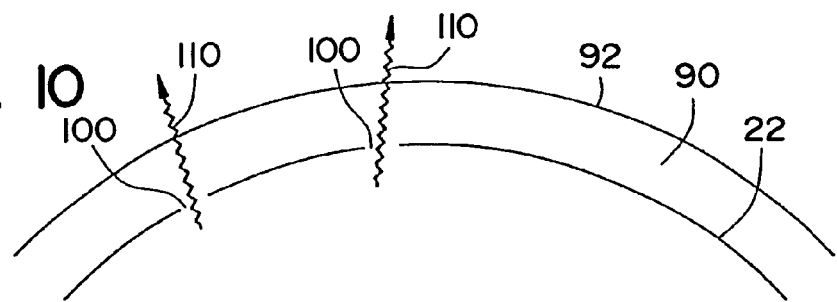
FIG. 10 is an enlarged sectional view of the surface of the prosthetic implant illustrating a coating material applied to an outer surface of the body of the prosthetic implant that has a plurality of openings.
Figure 11:
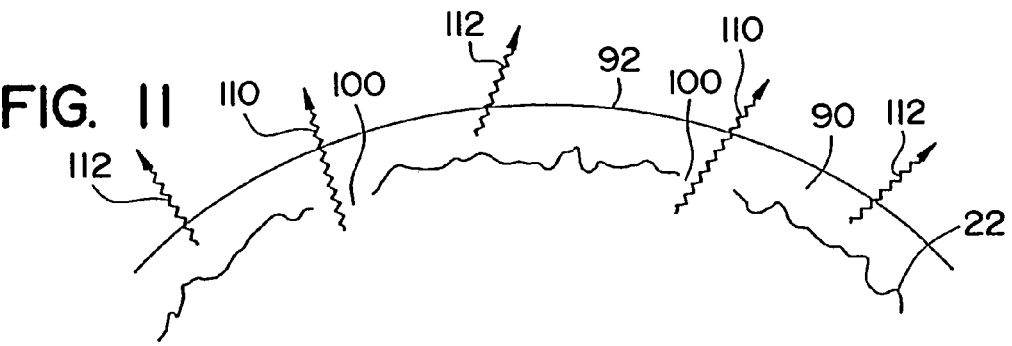
FIG. 11 is an enlarged sectional view of the surface of the prosthetic implant illustrating a coating material applied to a non-smooth outer surface of the body of the prosthetic implant that has a plurality of openings.
Figure 12:
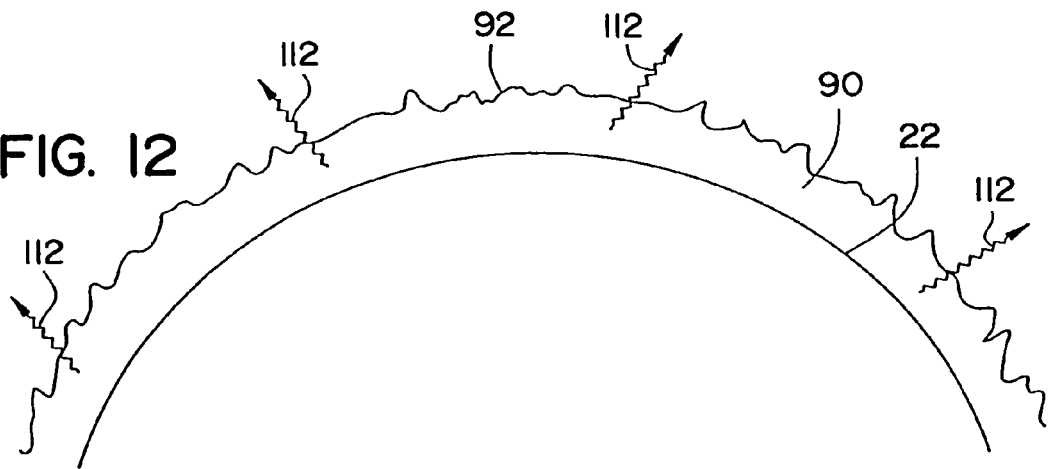
FIG. 12 is an enlarged sectional view of the surface of the prosthetic implant illustrating a coating material having a non-smooth surface applied to the outer surface of the body of the prosthetic implant.

Referring now to FIGS. 9-12, the body of the prosthetic implant is shown to have an outer surface 22 that is at least partially coated with a coating material 90. As can be appreciated, the outer surface of the stabilizer can also or alternatively be partially coated with a coating material. Coating material 90 can form a substantially smooth outer surface 92 as shown in FIGS. 9-11 or form a non-smooth surface 92 as shown in FIG. 12. Coating material 90 can be made of a variety of materials. Typically, coating material 90 includes one or more materials that are different from the material composition of the outer surface 22 of spherical body 20 and/or the stabilizer. Coating material 90 can also have a variety of functions such as, but not limited to, forming a substantially smooth surface over a substantially smooth outer surface as shown in FIG. 9, forming a substantially smooth surface over a substantially smooth outer surface and at least partially cover openings in the surface of spherical body 20 and/or the stabilizer as shown in FIG. 10, forming a substantially smooth surface of the prosthetic implant over a non-smooth outer surface and to at least partially cover openings 100 in the surface of spherical body 20 and/or the stabilizer as shown in FIG. 11, or forming a non-smooth surface over a substantially smooth outer surface 22 of spherical body 20 and/or the stabilizer as shown in FIG. 12. As can be appreciated, the coating material can perform other functions.

As shown in FIG. 10, the coating material is illustrated as allowing one or more biologically active substances and/or biologically inactive substances 110 to pass from opening 100 and through the coating material 90. As can be appreciated, the coating material can be formulated to prevent one or more biologically active substances and/or biologically inactive substances from passing through the coating material, and/or allowing one or more materials to pass through the coating material and into one or more of the openings. Coating material 90 can be formulated to control the flow rate of substance and/or materials out of and/or into opening 100. Typically, biologically active substances are used, among other purposes, to facilitate in the formation of a graft between one or more vertebrae, to promote bone and/or other tissue growth, to inhibit the rejection of the prosthetic implant, to reduce infection, to reduce inflammation, to reduce pain, to promote healing of surrounding tissue, to function as a location and/or visual indicator, and/or the like. As can be appreciated, one or more biologically neutral substances (e.g., water, inert or substantially inert compounds, etc.) can also be used to facilitate in the formation of a graft between one or more vertebrae, to promote bone and/or other tissue growth, to inhibit the rejection of the prosthetic implant, to reduce infection, to reduce inflammation, to reduce pain, to promote healing of surrounding tissue, to function as a location and/or visual indicator, and/or the like.

Referring now to FIGS. 11 and 12, coating material 90 includes at least one biologically active substance 112 that is released from the coating material. Such biologically active substances can be used, but are not limited to, to facilitate in the formation of a graft between one or more vertebrae, to promote bone and/or other tissue growth, to inhibit the rejection of the prosthetic implant, to reduce infection, to reduce inflammation, to reduce pain, to promote healing of surrounding tissue, to function as a location and/or visual indicator, and/or the like.

In view of the various configurations of the prosthetic implant illustrated in FIGS. 3-12, the generally spherical or ellipsoidal body of the prosthetic implant can include one or more outer surface regions that inhibit or prevent bone growth and/or other tissue growth on the outer surface, or promote bone growth and/or other tissue growth on the outer surface. One or more regions of the outer surface region can be a substantially smooth outer surface, a non-smooth outer surface or combination thereof. The non-smooth surfaces can include, but are not limited to, ridges, ribs, grooves, pits, notches, semi-matte, slits, slots, channels, corrugations, and/or the like. The reduction or prevention of bone growth and/or other tissue growth on the outer surface of the prosthetic implant can facilitate in allowing the generally spherical or ellipsoidal body to move freely or relatively freely between two vertebrae. The growth of bone or other tissue on and/or into the generally spherical or ellipsoidal body can result in the generally spherical or ellipsoidal body becoming seized or at least partially retained in a position relative to one or both vertebrae. This can be problematic if such seizure or partial retention is not desired. The outer surface of the generally spherical or ellipsoidal body can include a wear resistant material. The outer surface can have low frictional characteristics to allow for better movement between one or more vertebrae and/or to facilitate in the insertion and/or positioning of a prosthetic implant between one or more vertebrae. The one or more outer surface regions that inhibit or prevent bone growth and/or other tissue growth can have a total surface area that represents at least the majority or less than a majority of the total outer perimeter surface area of the generally spherical or ellipsoidal body. The one or more outer surface regions of the prosthetic implant can include a coating material. The coating material can at least partially form a substantially smooth outer surface and/or a non-smooth surface on the prosthetic implant. One or more layers of the coating material can be applied to the prosthetic implant. If more than one layers of coating material are applied, the each layer of the coating material can be formed of the same material or include one or more different materials. A uniform composition of the coating material can be applied to the prosthetic implant, or one or more portions of the prosthetic implant can include coating materials having non-uniform compositions. The thickness of the one or more layers of the coating material can be the same or different on one or more regions of the outer surface of the generally spherical or ellipsoidal body. The coating material can be a biocompatible material. Various polymers and/or copolymers can be included in the coating material to at least partially secure the coating material to the outer surface of the generally spherical or ellipsoidal body. The coating material can be at least partially secured to the generally spherical or ellipsoidal body by adhesive bonding, welding, brazing, soldering, shrink wrapping, melting, spray coating, hop dipping, electroplating, immersion coating, brush coating, and/or the like. At least a portion of the coating material can be biologically neutral. At least a portion of the coating material can include one or more biological substances that are biologically neutral and/or biologically active. Various substances that can be included in the coating (biologically neutral and/or biologically active) include, but are not limited to, natural and/or synthetic bone cement; urethane foam; epoxy compounds; pharmaceuticals to diminish pain, to stimulate bone growth, to inhibit bone growth, to promote tissue growth, to inhibit tissue growth, to inhibit rejection, to inhibit inflammation, to reduce and/or prevent infection, etc. (e.g., autologous growth compound; bone; polyglycolate polymers or analogues; lactides; polydioxamone; polyglycolate; lactide/glycolide copolymers; antithrombogenic agents; steroids; seraminr and/or derivatives thereof; thioprotese inhibitors; nitric oxide; ibuprofen; aspirin, antimicrobials; antibiotics; tissue plasma activators; monoclonal antibodies; antifibrosis compounds; growth factors Interferons; steroids; penicillins; cephalosporins; aminoglycosides; anti-depressants anti-mitotic agents; sense or antisense oligonucleotides (e.g., DNA, RNA, plasmid DNA, plasmid RNA, nucleic acid analogues (e.g., peptides nucleic acids); inhibitors; radioactive agents; toxins; growth factors; oligonucleotides; antiplatlet compounds; antitabolite compounds; anti-inflammatory compounds; anticoagulent compounds; antimitotic compounds; antioxidants; antimicrobials; antibiotics; antimetabolite compounds; anti-migratory agents; anti-matrix compounds; protein kinase inhibitors; anti-vital compounds; anti-fungal compounds; anti-protozoal compounds; tissue plasma activators; monoclonal antibodies; antifibrosis compounds; hormones; anti-proliferatives; anti-platelet compounds; metabolic inhibitors; antineoplastics; proliferation inhibitors; cytotoxic compounds; anti-coagulants; fribrinolytics; thrombin inhibitors; antimitotics; antitumor compounds; cholesterol-lowering agents; vasodilating agents; anti-sense oligonucleotides; human tissue; animal tissue; synthetic tissue; human cells; animal cells; synthetic cells; hydroxyapatite bone and/or proteins; cartilage activation factor; bone-stimulation matter; bone-growth matter; bone activating matter; tissue-stimulation matter; tissue-growth matter; tissue activating matter; bone growth inhibitors; bone growth promoters, tissue growth promoters; tissue growth inhibitors; rejection inhibitors; etc.) As can be appreciated, the biologically neutral and/or biologically active substances can include other compounds. The coating material can include one or more biologically active substances that can migrate from the coated material and/or dissociate from the coating material into the surrounding tissue. The one or more biologically active substances included in the coating material can be immediately or substantially immediately released into the surrounding tissue during and/or after the prosthetic implant is inserted between the vertebrae, or released in a delayed fashion after the prosthetic implant is inserted between the vertebrae. The delayed release can be a uniform or varied release. The rate of release can be varied on the type of biologically active substance being released and/or the location of release on the prosthetic implant. The delayed release of one or more biologically active substances can be accomplished by one or more mechanisms such as, but not limited to, 1) the at least partial entrapping or encapsulating of one or more biologically active substances in a dissolvable material in the coating material, 2) covalent and/or ionic bonding of one or more biologically active substances to one or more other coating materials, etc. The coating material can include one or more substances that enhance the strength and/or durability of the prosthetic implant and/or hardens or softens the surface of the prosthetic implant. The generally spherical or ellipsoidal body of the prosthetic implant can include one or more recesses and/or openings to promote or inhibit bone growth and/or other tissue growth on the surface of and/or into the interior of the generally spherical or ellipsoidal body of the prosthetic implant. The one or more recesses and/or openings can be at least partially coated with a coating material. The generally spherical or ellipsoidal body can include one or more internal cavities. These cavities can include one or more passageways to the outer surface of the generally spherical or ellipsoidal body thereby terminating at an opening on the outer surface of the generally spherical or ellipsoidal body, or be substantially isolated from the outer surface of the generally spherical or ellipsoidal body. At least one of the cavities can be substantially vacant or include one or more biologically active and/or biologically neutral substances. The one or more of the cavities in the generally spherical or ellipsoidal body can allow blood supply and/or other body fluids to flow into and/or out of one or more of the cavities. The size or the passageway and/or opening to the outer surface of the generally spherical or ellipsoidal body can be selected to control the amount and/or rate of the one or more biologically active substances in the one or more cavities that exit the cavities. The size of the passageway and/or opening to the outer surface of the generally spherical or ellipsoidal body can be selected to control the amount and/or rate of bone and/or other tissue growth that occurs in the opening and/or passageway and/or into the one or more cavities. The one or more biologically active and/or biologically neutral substances in the one or more cavities can be at least partially packed in the cavity prior to, during and/or after the insertion of the prosthetic implant between one or more vertebrae. The volume of each of the one or more cavities in the generally spherical or ellipsoidal body is less than the total volume of the generally spherical or ellipsoidal body. When the generally spherical or ellipsoidal body includes two or more cavities, a plurality of the cavities can have the same or different volumes. At least two of the cavities in the generally spherical or ellipsoidal body can be fluidly connected to one another. Each of the one or more cavities can have a variety of shapes and/or sizes. The generally spherical or ellipsoidal body of the prosthetic implant can include one or more openings in the outer wall of the generally spherical or ellipsoidal body of the prosthetic implant to facilitate in the positioning of the prosthetic implant between the vertebrae, to secure the prosthetic implant in place within the intervertebral disc space and/or to connect one or more components of a spine stabilization system to the prosthetic implant (e.g., cage, plate, screw, rod, nail, post, etc.). One or more of the openings in the outer wall of the generally spherical or ellipsoidal body can be designed to receive an instrument for guiding and/or inserting the prosthetic implant between the vertebrae of the spine by an anterior, posterior, lateral, and/or latroscopic approach into the spinal column. At least one opening can include a securing mechanism such as, but not limited to, a thread, in the opening to secure the instrument within the opening. One or more openings in the outer wall of the generally spherical or ellipsoidal body of the prosthetic implant can be at least partially closed and/or sealed prior to, during and/or after the prosthetic implant is inserted between one or more vertebrae. A cap can be used to at least partially close and/or seal one or more openings in the generally spherical or ellipsoidal body. The cap can alter the size of the one or more openings to at least partially control the amount and/or rate of biologically active substance exits the one or more openings, and/or to at least partially control the rate and/or amount of materials (e.g., bone, tissue, etc.) entering the opening. The cap can be made of a porous material or a non-porous material. The cap includes a sealable or non-sealable opening that is used to provide a passageway through the cap to insert one or more biologically active and/or biologically neutral substances through the cap and into the body of the prosthetic implant. The opening in the cap can include a sealable material that allows a syringe to be inserted through the material so that one or more biologically active and/or biologically neutral substances can be inserted into the prosthetic implant and which reseals the opening when the syringe is removed. The cap can be designed to receive an instrument for guiding and/or inserting the cap into one or more openings in the generally spherical or ellipsoidal body; and/or be connected to one or more comments of a stabilization system. The cap can be made of a biocompatible material. The cap can be made of or include a material that is the same or different as the material that forms the generally spherical or ellipsoidal body. At least one or more surfaces of the prosthetic implant can be rounded off and/or smoothed so as not to be sharp. Rounding off the surfaces reduces and/or eliminates pinching of the nerve leading from the spinal cord which can result in pain, damage and/or paralysis to the individual. The rounded and/or smoothed surfaces avoid or minimize nerve pressure that can be exerted on the nerves intervertebrally exiting the spinal cord. The one or more rounded off and/or smoothed surfaces can also facilitate with the insertion of the prosthetic implant within the intervertebral disc space.

The prosthetic implant can include at least one stabilizer that expands at least partially about the generally spherical or ellipsoidal body of the prosthetic implant. The stabilizer is designed to facilitate in at least partially orienting the prosthetic implant between one or more vertebrae, to limit the amount of movement of the generally spherical or ellipsoidal body between one or more vertebrae and/or facilitate in the insertion of the prosthetic implant between one or more vertebrae. The at least one stabilizer can be positioned substantially about the central axis of the generally spherical or ellipsoidal body or positioned substantially off-center of the central axis of the generally spherical or ellipsoidal body. The stabilizer can be substantially disc shaped; however, the shape of the stabilizer is in no way limited to such a shape. The stabilizer can extend a substantially uniform or non-uniform distance from the outer surface of the generally spherical or ellipsoidal body of the prosthetic implant. One or more portions of the stabilizer can extend from the outer surface of the generally spherical or ellipsoidal body of the prosthetic implant a distance of up to about 300% the maximum diameter of the spherical or ellipsoidal body. Typically the stabilizer extends at least about 0.0005 mm from the outer surface of the generally spherical or ellipsoidal body of the prosthetic implant; however, other distances can be used. The maximum thickness of the stabilizer is less than the maximum diameter of the generally spherical or ellipsoidal body of the prosthetic implant (e.g., 0.001-99% of the maximum diameter of the generally spherical or ellipsoidal body). The thickness of the stabilizer can be substantially constant or vary along the radial width of the stabilizer. The reduction in thickness can be a constant or variable thickness reduction. The stabilizer can include one or more tapered edges. The stabilizer can be at least partially made of a porous material, a non-porous material, a non-biodegradable material, and/or a biodegradable material (e.g., bone, synthetic bone, stainless steel, titanium, chromemolybdenum, cobalt chromium alloy, ceramic (zirconium oxide ceramic, aluminum oxide ceramic, etc.), chrome or chrome alloys, cobalt or cobalt alloys, polycarbonate, polypropylene, polyethylene, polymethylmethacrylate, polysolfone types filled with glass and/or carbon fibers, and/or various types of carbon and fiber reinforced polymers). The stabilizer can be coated with and/or contain one or more biologically active and/or biologically neutral substances. Such biologically active and/or biologically neutral substances can be used, but are not limited to, to facilitate in the formation of a graft between one or more vertebrae, to promote bone and/or other tissue growth, to inhibit the rejection of the prosthetic implant, to reduce infection, to reduce inflammation, to reduce pain, to promote healing of surrounding tissue, to function as a location and/or visual indicator, and/or the like. The stabilizer can include a wear resistant material. The stabilizer can include a material that has an increased or decreased frictional coefficient. The stabilizer and/or a coating that are at least partially coated on the stabilizer can result in at least a portion of the outer surface of the stabilizer having a smooth surface, a rough surface, a low frictional surface, a wear resistant surface, and/or the like. The types of materials used to form the stabilizer and/or the types of materials of the coating materials that can be applied to one or more portions of the stabilizer can be the same as, similar to, or different than the materials that are included in the generally spherical or ellipsoidal body of the prosthetic implant and/or materials of the coating material used on the generally spherical or ellipsoidal body of the prosthetic implant. The manner in which one or more layers of the coating material are applied to the stabilizer can be the same or different from the manner in which one or more layers of coating materials can be applied to the generally spherical or ellipsoidal body of the prosthetic implant. The stabilizer can include one or more openings and/or cavities. The openings and/or cavities can include various types of biologically active and/or biologically neutral substances. Such biologically active and/or biologically neutral substances can be used, but are not limited to, to facilitate in the formation of a graft between one or more vertebrae, to promote bone and/or other tissue growth, to inhibit the rejection of the prosthetic implant, to reduce infection, to reduce inflammation, to reduce pain, to promote healing of surrounding tissue, to function as a location and/or visual indicator, and/or the like. The stabilizer can include one or more layers of a coating material that includes one or more biologically active substances that migrate from the coating material and/or dissociate from the coating material into the surrounding tissue. The one or more biologically active substances that are inserted in, entrapped in and/or at least partially bonded to the coating material can have an at least partially controlled time release and/or an immediate release rate of the one or more biologically active substances into the surrounding tissue. The coating material can enhance the strength and/or durability of the stabilizer and/or hardens or softens the surface of the stabilizer. The stabilizer can be detached from, or is substantially permanently connected to, the generally spherical or ellipsoidal body of the prosthetic implant. The stabilizer and the generally spherical or ellipsoidal body can constitute a single or multiple components. The angle of articulation of the stabilizer in relation to the outer surface of the generally spherical or ellipsoidal body can be constant or vary from an angle of less than about 0.01° to about 180°. The stabilizer can be at least partially expanded prior to, during and/or after the prosthetic implant is at least partially inserted between two vertebrae. The amount of expansion can be a predetermined or set amount, or a non-predetermined or variable amount.

The generally spherical or ellipsoidal body of the prosthetic implant can be formed from a single piece or a plurality of pieces. Each of the pieces can have the same or different shape, size, material composition, physical properties, number of cavities, surface morphology, openings, internal components, etc. An expandable material that can be used to at least partially form a stabilizer can be positional between two or more pieces of the generally spherical or ellipsoidal body of the prosthetic implant. The expandable material can include an elastic sack or pouch designed to at least partially receive a material that causes the sack or pouch to at least partially expand, and/or the expandable material can be a malleable or moldable material that can be at least partially expanded by one or more mechanisms (e.g., exposure to heat, exposure to pressure, chemical reaction, exposure to electrical current, exposure to electromagnetic waves, exposure to magnetic waves, etc.). The expandable material can be permanently or releasably connected to one or pieces of the generally spherical or ellipsoidal body of the prosthetic implant by one or more mechanisms (e.g., adhesive and/or other type of chemical bond, melted bond, mechanical connection (i.e., tack, nail, screw, wire, cord, clamp, clip, hook, dowel, rivet, bolt, pin, seam, hook and loop fasteners, etc.), magnetic connection, expansion of the expandable material into one or more channels, cavities, etc. of the one or more pieces of the generally spherical or ellipsoidal body, etc. The two or more pieces of the generally spherical or ellipsoidal body can be permanently or releasably connected together by one or more mechanisms (e.g., adhesive and/or other type of chemical bond, melted bond, mechanical connection (i.e., tack, nail, screw, wire, cord, clamp, clip, hook, dowel, rivet, bolt, pin, seam, hook and loop fasteners, etc.), magnetic connection, etc.). The connection between the two or more pieces of the generally spherical or ellipsoidal can allow, prevent or restrict relative movement between the two of more pieces. When one stabilizer is to be formed, the expandable material can be positioned at least closely adjacent to or away from the central axis of the body of the generally spherical or ellipsoidal body of the prosthetic implant. When two or more stabilizers are formed, the two or more expandable material sections can be positioned in different regions on the body of the generally spherical or ellipsoidal body. The radial axis of the plurality of stabilizers in an expanded state can be parallel or nonparallel. A portion of the generally spherical or ellipsoidal body of the prosthetic implant can be expandable and/or contractable. The expanding or contracting of one or more portions of the generally spherical or ellipsoidal body can result in an increase in size and surface area or a decrease in size and surface area of the prosthetic implant. The expansion and/or contraction of one or more portions of the generally spherical or ellipsoidal body can be used to facilitate in the insertion and/or positioning of the prosthetic implant between two vertebrae. If the generally spherical or ellipsoidal body is formed of two or more pieces, one or more of the pieces can be designed to expand and/or contract. The expansion and/or contraction of at least one or more one or more portions of the generally spherical or ellipsoidal body can occur at the same or a different time from the expansion of the stabilizer. The amount of increase and/or decrease of expansion/contraction of the generally spherical or ellipsoidal body can be substantially uniform or vary. The mechanism by which one or more portions of the generally spherical or ellipsoidal body can be expanded and/or contracted are typically similar to the one or more mechanisms that can be used to expand the stabilizer; however, other mechanism can be used. The expandable and/or contractable portions of the generally spherical or ellipsoidal body can include one or more materials that can be used in the expandable stabilizer. As can be appreciated, the at least partial expansion and/or contraction of one or more portions of the generally spherical or ellipsoidal body can occur prior to, during and/or after the insertion of the prosthetic implant between the vertebrae.

The prosthetic implant can include one or more pressure sensors used to monitor the pressure being applied to one or more portions or regions of the prosthetic implant prior to, during and/or after the at least partial insertion of the prosthetic implant between the vertebrae, and/or during and/or after the expansion of the stabilizer and/or body. The monitoring of the pressure being applied to one or more regions of the prosthetic implant can be used to a) facilitate in determining that the proper size of the prosthetic implant has been selected; b) facilitate in confirming that the prosthetic implant is made of the proper materials for a particular procedure; c) monitor the expansion of the stabilizer to facilitate in ensuring that it has not been over or under expanded, and if so, cause the stabilizer to contract if so desired; d) monitor the expansion of the body of the prosthetic implant to facilitate in ensuring that it has not been over or under expanded and if so, cause the stabilizer to contract/expand if so desired; e) monitor the stresses and/or pressures on the prosthetic implant to determine whether it is holding up, working properly, has become dislocated, has become damaged, etc.; f) monitor the wear on the prosthetic implant; g) monitor the healing and/or damage of the surrounding tissue; and/or monitor the operation of the prosthetic implant. The information obtained from the one or more pressure sensors can be periodically obtained or downloaded, or continuously obtained or downloaded. The information obtained or downloaded from the one or more pressure sensors can be manually and/or electronically analyzed (e.g., a computer program, etc.). As can be appreciated, other and/or additional uses of the pressure information are contemplated by the invention. The one or more pressure sensors can be located on one or more surface locations on the body and/or stabilizer, and/or be at least partially positioned or embedded in one or more locations on the body and/or stabilizer. The one or more pressure sensors can include visual and/or sound indicators to provide information about the pressure being detected. The one or more pressure sensors can also or alternatively transmit (by wire, cable, fiberoptics, wirelessly, etc.) and/or store information about the pressure being detected. The wireless transmission can be by one or more types of electromagnetic waves, magnetic waves, and/or sound waves.

Referring now to FIGS. 13-16, there are illustrated a few of the various mechanisms by which the stabilizer can be at least partially expanded to a desired shaped and/or size. As illustrated in FIGS. 13-16, the stabilizer can be at least partially expanded by one or more mechanisms. Such mechanisms include, but are not limited to, expansion by insertion of a fluid into the prosthetic implant, use of one or more memory metals to cause expansion of one or more components of the prosthetic implant, expansion by chemical reaction of one or more components of the prosthetic implant, expansion by a compression force on one or more materials of the prosthetic implant, etc. One or more of these mechanisms can be implemented in a variety of ways. For instance, the at least partial expansion by insertion of fluid can be accomplished by 1) externally directing a fluid (e.g., liquid, gas, etc.) by a hydraulic device (e.g., syringe, pump, etc.) into one or more regions of the prosthetic implant until the desired amount of expansion of the stabilizer has been achieved, and/or 2) internally directing a fluid (e.g., liquid, gas, malleable and/or moldable compound (i.e., hardenable polymer, polymer paste, etc.), etc.) by a hydraulic device (e.g., pump, etc.) located on and/or within the prosthetic implant to cause the fluid to flow into one or more internal channels and/or cavities in the prosthetic implant until the designed amount of expansion of the stabilizer has been achieved. As can be appreciated, other mechanisms for expansion by insertion of fluid can additionally or alternatively be used. At least partial expansion by use of one or more memory metals can be accomplished by the inclusion of one or more memory materials (e.g., metal, polymer, etc.) which may or may not have the same composition, in one or more regions of the prosthetic implant and to cause the memory material to at least partially revert to a memory location by the used of heat, electric current, electromagnetic waves, sound waves, etc. so as to cause the stabilizer to expand until the desired amount of expansion has been achieved. As can be appreciated, other mechanisms for expansion by use of one or more memory materials can additionally or alternatively be used. At least partial expansion by use of a chemical reaction of one or more components can be accomplished by inserting (e.g., by syringe, by pump, etc.) one or more reactants and/or catalyzing agents into one or more regions of the prosthetic implant to cause a chemical reaction to occur which results in the expansion of the stabilizer. The reaction can be cause to occur as a result of the mere introduction of the one or more reactants and/or catalyzing agents into the prosthetic implant, and/or can be caused to occur and/or accelerate by the introduction of heat, electric current, magnetic waves, electromagnetic waves, sound waves, etc. The expansion from the chemical reaction can be due to the formation of one or more chemical compounds having increase volumes (e.g., urethane foams, etc.) and/or from the result of a restructuring of one or more compounds that have increased volumes. The expansion by use of a chemical reaction of one or more components could also or alternatively be accomplished by internally inserting (e.g., by pump positioned on and/or within a prosthetic implant, etc.) one or more reactants and/or catalyzing agents into one or more channels or cavities of the prosthetic implant to cause a chemical reaction to occur which results in the expansion of the stabilizer. As can be appreciated, other mechanisms for expansion by use of chemical reaction can additionally or alternatively be used. At least partial expansion by a compression force on one or more materials of the prosthetic implant can be accomplished by 1) the compressive forces applied by the vertebrae on the prosthetic implant during and/or after the prosthetic implant is at least partially inserted between the vertebrae which causes a malleable, moldable and/or fluid material to flow outwardly from the body of the prosthetic implant until the designed amount of expansion of the stabilizer has been achieved; 2) mechanically compressing one or more portions of the prosthetic implant together by a screw, clamp, rod insertion, magnets, etc. which causes a malleable, moldable and/or fluid material to flow outwardly from the body of the prosthetic implant until the designed amount of expansion of the stabilizer has been achieved. As can be appreciated, other mechanisms for expansion by use of compressive forces can additionally or alternatively be used. In one or more non-limiting expansion mechanisms discussed above, the expanded stabilizer and/or one or more components in the expanded stabilizer can be set and/or at least partially hardened by one or more mechanisms (e.g., natural drying, chemical reaction (by heat, by electric current, by sound waves, by electromagnetic waves, by introduction of one or more catalysts and/or reactants, magnetic waves, etc.)). The expandable material can include, but is not limited to, an elastic or flexible sack or pouch designed to at least partially receive a material that causes the sack or pouch to at least partially expand, and/or the expandable material can be a malleable or moldable material (e.g., cement material, epoxy material, thermoplastic material, elastomers, thermoset materials, photocurable resins, thermosetting resins, etc.) that can be at least partially expanded by one or more mechanisms (e.g., exposure to heat, exposure to pressure, chemical reaction, exposure to electrical current, exposure to electromagnetic waves, exposure to magnetic waves, memory metal or polymer, etc.).

Figure 13:
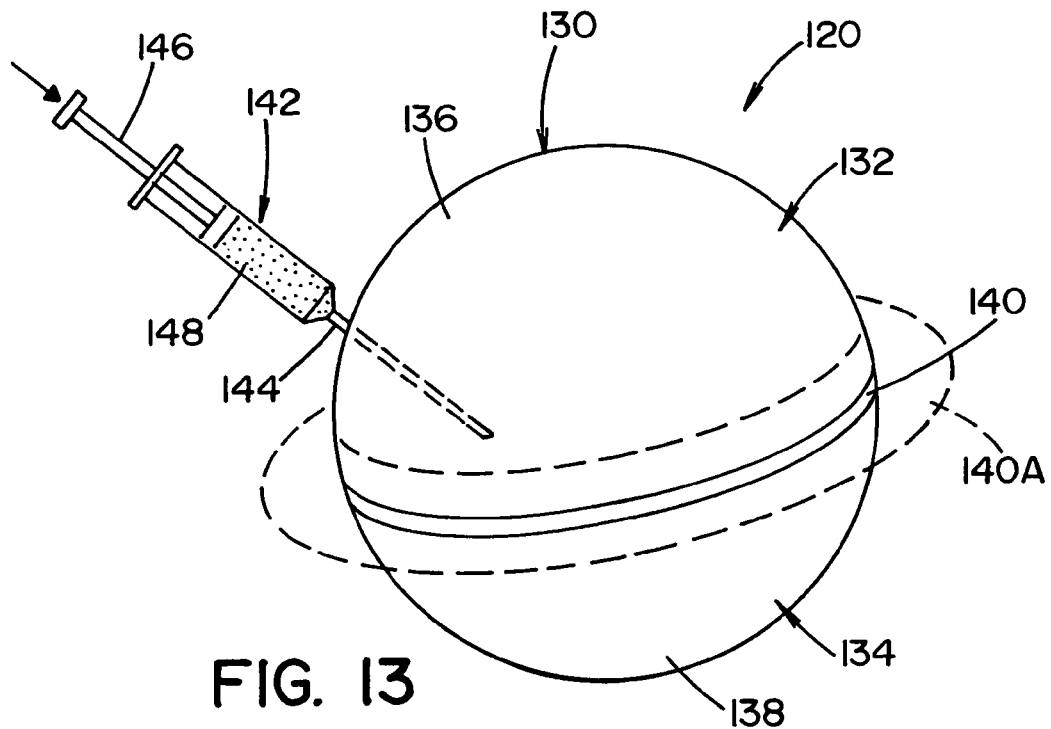
FIG. 13 is an enlarged perspective view of the prosthetic implant of the present invention illustrating the expansion of a stabilizer by one type of mechanism.
Figure 18:
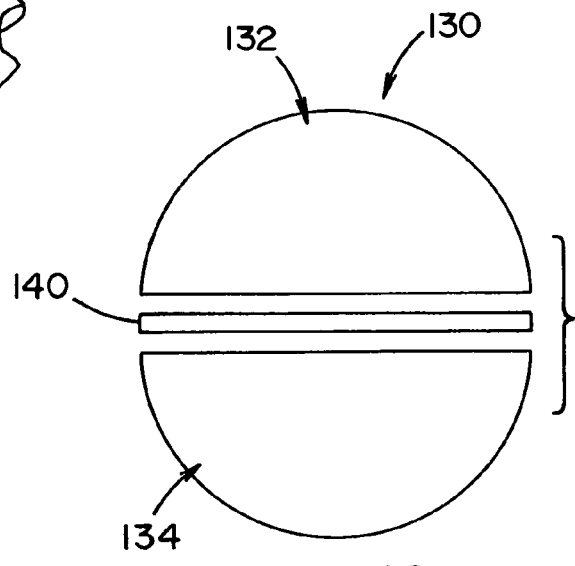
FIG. 18 is an enlarged perspective view of the prosthetic implant of the present invention illustrating the prosthetic implant formed from three components.

Referring specifically to FIG. 13, there is illustrated a prosthetic implant 120 that includes a spherical body 130 formed of two semi-hemispherical sections 132, 134, each of which have an outer surface 136, 138, respectively. Prosthetic implant 130 also includes an expandable stabilizer 140 connected to spherical body 130. The stabilizer and the two semi-hemispherical sections form three distinct components of the prosthetic implant as illustrated in FIG. 18. Typically the two semi-hemispherical sections are made of a durable material that resist deformation when exposed to compressive forces. The one or more materials forming the stabilizer can also be made of a durable material. The material forming the stabilizer is generally different from the two semi-hemispherical sections, in that the material forming the two semi-hemispherical sections is generally set in shape, whereas the material forming the stabilizer is expandable, flowable, malleable, etc. The stabilizer can include an elastic sack or pouch that contains and/or receives one or more materials. Additionally or alternatively, the stabilizer can include elastic walls that are connected to the two semi-hemispherical sections to form a cavity between the two semi-hemispherical sections so as to contain and/or can receive one or more materials. The one or more materials contained in or to be received are selected to cause the sack or pouch or walls to expand under certain conditions (e.g., internal pressure, deformation, growth due to a reaction, etc.) to at least partially form the expanded stabilizer. The stabilizer can include a viscous material that does not need to be, but can be, contained within an elastic material. The viscous material typically is a malleable material and/or expandable material that deforms and/or expands under certain conditions to at least partially form the expanded stabilizer. Stabilizer 140 is illustrated in a non-expanded condition. The outer perimeter of stabilizer 140 is illustrated as substantially flush with the outer surface of the two semi-hemispherical sections. It can be appreciated that at least a portion of the outer perimeter of the stabilizer can be recessed from an outer surface of the two semi-hemispherical sections and/or extend outwardly from the outer surface of the two semi-hemispherical sections. A syringe 142 is illustrated being used to injecting a material 148 through needle 144 into the interior of one of the two semi-hemispherical sections by depressing plunger 146 as indicated by the arrow. As can be appreciated, the syringe could inject a material into the interior of the other semi-hemispherical sections, both semi-hemispherical sections and/or the stabilizer. As can also be appreciated, other devices could be used for the injection of the materials. The injection of the material into the prosthetic implant can be through the outer wall of the body and/or stabilizer, or through an opening in the body or stabilizer. As can be appreciated, a cap could be inserted over an opening, which cap could be designed to receive the needle of the syringe. In such a configuration, the cap would allow materials into the opening and inhibit or prevent the materials to flow out of the opening after the needle was removed from the cap. The material inserted into the body of the prosthetic implant can be a biologically neutral substance (e.g., water, saline water, inert liquid, etc.), a biologically active substance, and/or a chemical reactant and/or catalyst. The consistency of the injected materials can vary widely (e.g., about the viscosity of water (1 cps @ 70° C.) to the viscosity of a thick gel, putty or caulk (150,000-100,000,000+ cps @ 70° C.)). The insertion of a biologically active and/or biologically neutral substance can be used to cause the stabilizer to expand due to internal pressure forces from the insertion of the materials being applied on the stabilizer. Materials can be injected until the stabilizer has expanded to a desired size and/or shape as shown by reference numeral 140A. The insertion of a chemical reactant and/or catalyst can be used to cause a reaction to occur that can a) cause at least partial hardening and/or solidification of an expanded stabilizer, and/or b) cause at least partial expansion of the stabilizer. The inserted chemical reactant and/or catalyst can be designed to react with one or more materials already contained in the stabilizer, or all the reactant materials can be inserted in the stabilizer for immediate or subsequent reaction. As can be appreciated, the chemical reaction can be at least partially induced by electric current, electromagnetic waves, sound waves, heat, magnetic waves, etc. The amount of chemical reactant and/or catalyst inserted can be used to control the amount of expansion of the stabilizer. The chemical reaction can be selected to form an expanding product which in turn causes the stabilizer to expand due to internal pressure forces from the expanding product. After stabilizer 140A has expanded to a desired shape and/or size, the expanded stabilizer can be hardened, if desired, by allowing the materials in the stabilizer to naturally harden and/or to induce hardening by the use of heat, electric current, electromagnetic waves, sound waves, magnetic waves, and/or chemical reaction. Expanded stabilizer 140A is illustrated as disc shaped and extending about the central axis of spherical body 130; however, it will be appreciated that the stabilizer can have other shapes and/or be positioned in other locations on the body.

Figure 14:
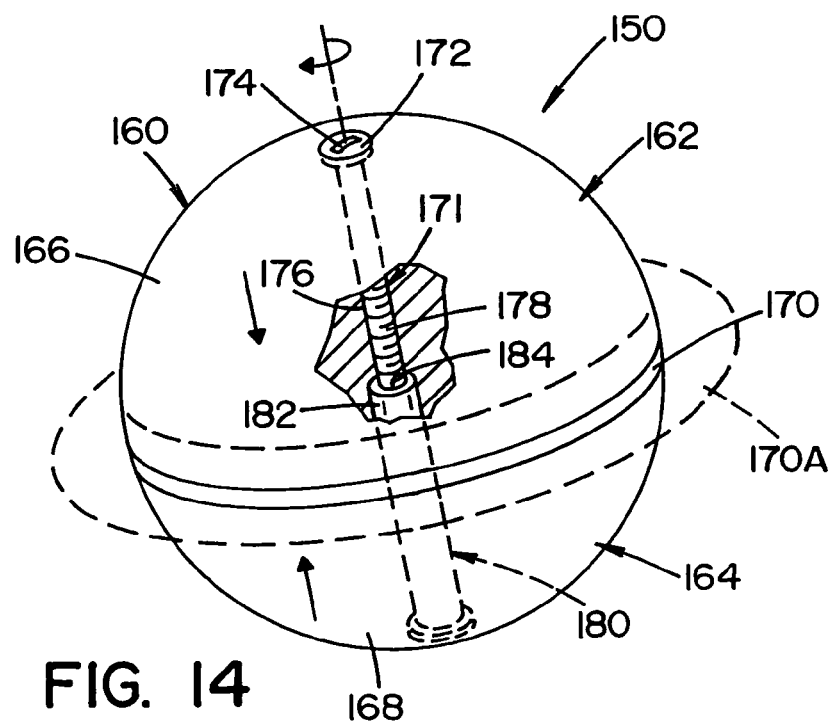
FIG. 14 is an enlarged perspective view of the prosthetic implant of the present invention illustrating the expansion of a stabilizer by another type of mechanism.

Referring now to FIG. 14, there is illustrated a prosthetic implant 150 which includes a spherical body 160 formed of two semi-hemispherical sections 162, 164, each of which has an outer surface 166, 168, respectively. Prosthetic implant 150 also includes an expandable stabilizer 170 connected to spherical body 160. The stabilizer and the two semi-hemispherical sections form three distinct components of the prosthetic implant as illustrated in FIG. 18. Typically the two semi-hemispherical sections are made of a durable material that resists deformation when exposed to compressive forces. The one or more materials forming the stabilizer can be also made of a durable material; however, the material is designed to deform when exposed to external compressive forces and/or internal expansive forces. The deformation properties of the one or more materials forming the stabilizer enable the stabilizer to expand under certain circumstances. Stabilizer 170 is illustrated in a non-expanded condition. The outer perimeter of stabilizer 170 is illustrated as substantially flush with the outer surface of the two semi-hemispherical sections. It can be appreciated that at least a portion of the outer perimeter of the stabilizer can be recessed from an outer surface of the two semi-hemispherical sections and/or extend outwardly from the outer surface of the two semi-hemispherical sections. Semi-hemispherical section 162 is illustrated as including a threaded screw 171 having a slot 174 on the head 172 of the screw. The slot is designed to receive an instrument to rotate the screw. Screw 171 has one or more threads 178 on the body 176 of the screw. The body of the screw is designed to be threadedly received into a threaded cavity 184 on the body 182 of cylinder 180 located in semi-hemispherical section 164. As can be appreciated, the top of the cylinder can include a slot for rotation, or can be fixed in position. When screw 171 is rotated in the direction of the arrow, the body of the screw is threaded into the body of cylinder 180 thereby causing the two semi-hemispherical sections to move together and compress stabilizer 170. The compression of the stabilizer results in the expansion of the stabilizer to an expanded state as represented by reference number 170A. The one or materials that form the stabilizer can include materials having a consistency that widely varies (e.g., about the viscosity of water (1 cps @ 70° C.) to the viscosity of a thick putty or caulk (150,000-100,000,000 cps @ 70° C.)). After stabilizer 170A has been expanded to a desired shape and/or size, the expanded stabilizer can be hardened, if desired, by allowing the materials in the stabilizer to natural harden and/or to induce hardening by the use of heat, electric current, electromagnetic waves, sound waves, magnetic waves, and/or chemical reaction. Expanded stabilizer 170A is illustrated as disc shaped and extending about the central axis of spherical body 160; however, it will be appreciated that the stabilizer can have other shapes and/or be positioned in other locations on the body.

Figure 15:
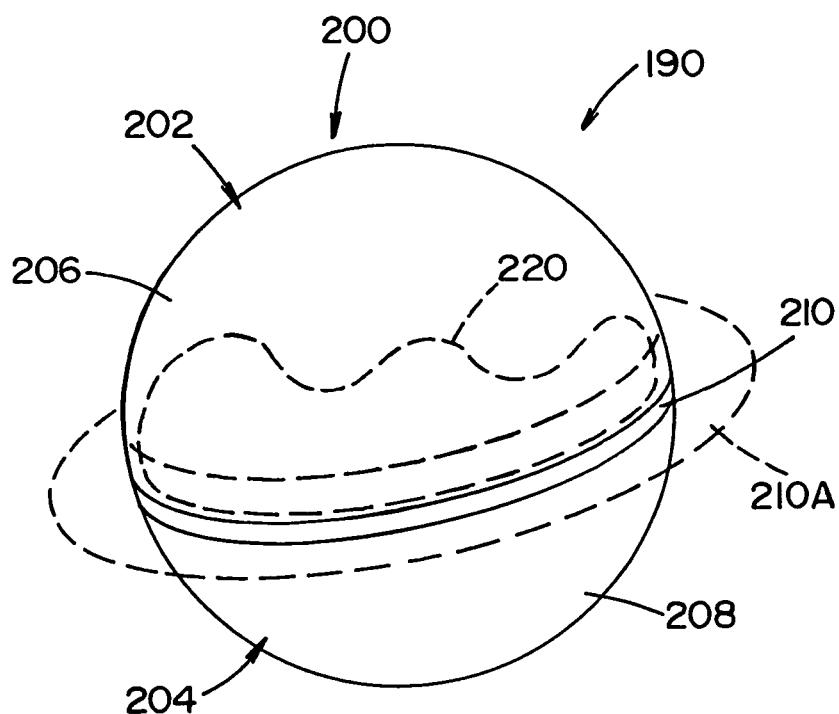
FIG. 15 is an enlarged perspective view of the prosthetic implant of the present invention illustrating the expansion of a stabilizer by still another type of mechanism.

Referring now to FIG. 15, there is illustrated a prosthetic implant 190 that includes a spherical body 200 formed of two semi-hemispherical sections 202, 204, each of which has an outer surface 206, 208, respectively. Prosthetic implant 190 also includes an expandable stabilizer 210 connected to spherical body 200. The stabilizer and the two semi-hemispherical sections form three distinct components of the prosthetic implant as illustrated in FIG. 18. Typically the two semi-hemispherical sections are made of a durable material that resist deformation when exposed to compressive forces. The one or more materials forming the stabilizer is also made of a durable material; however, the material is designed to deform when exposed to external compressive forces and/or internal expansive forces. The deformation properties of the one or more materials forming the stabilizer enable the stabilizer to expand under certain circumstances. Stabilizer 210 is illustrated in a non-expanded condition. The outer perimeter of stabilizer 210 is illustrated as substantially flush with the outer surface of the two semi-hemispherical sections. It can be appreciated that at least a portion of the outer perimeter of the stabilizer can be recessed from an outer surface of the two semi-hemispherical sections and/or extend outwardly from the outer surface of the two semi-hemispherical sections. Positioned within the stabilizer and/or within one or both semi-hemispherical sections is a memory material 220. The memory material typically is a type of memory metal and/or polymer. The shape of the memory material can widely vary. The memory material is designed to revert at least partially back to a memory position upon exposure to some stimuli (e.g., heat, electric current, sound wave, magnetic waves, electromagnetic waves, etc.). The reversion of the memory material to some memory position results in the memory material directly acting on the stabilizer (e.g., by contact) and/or by indirectly acting on the stabilizer (e.g., movement of memory material acting on another material which in turn acts on the stabilizer, etc.) to cause the stabilizer to expand to an expanded position as illustrated by reference number 210A. The one or materials that form the stabilizer can include materials having a consistency that widely varies (e.g., about the viscosity of water (1 cps @ 70° C.) to the viscosity of a thick putty or caulk (150,000-100,000,000 cps @ 70° C.)). After stabilizer 170A has expanded to a desired shape and/or size, the expanded stabilizer can be hardened, if desired, by allowing the materials in the stabilizer to natural harden and/or to induce hardening by the use of heat, electric current, electromagnetic waves, sound waves, magnetic waves, and/or chemical reaction. Expanded stabilizer 210A is illustrated as disc shaped and extending about the central axis of spherical body 200; however, it will be appreciated that the stabilizer can have other shapes and/or be positioned in other locations on the body.

Figure 16:
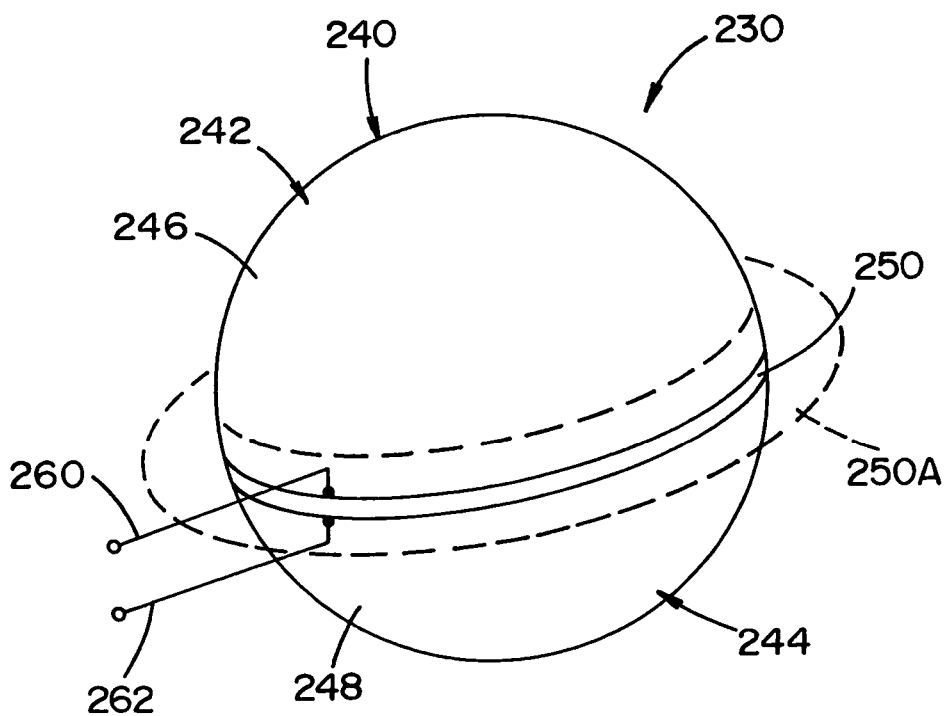
FIG. 16 is an enlarged perspective view of the prosthetic implant of the present invention illustrating the expansion of a stabilizer by yet another type of mechanism.

Referring now to FIG. 16, there is illustrated a prosthetic implant 230 that includes a spherical body 240 formed of two semi-hemispherical sections 242, 244, each of which has an outer surface 246, 248, respectively. Prosthetic implant 230 also includes an expandable stabilizer 250 connected to spherical body 230. The stabilizer and the two semi-hemispherical sections form three distinct components of the prosthetic implant as illustrated in FIG. 18. Typically the two semi-hemispherical sections are made of a durable material that resists deformation when exposed to compressive forces. The one or more materials forming the stabilizer is also made of a durable material; however, the material is designed to deform when exposed to external compressive forces and/or internal expansive forces. The deformation properties of the one or more materials forming the stabilizer enable the stabilizer to expand under certain circumstances. Stabilizer 250 is illustrated in a non-expanded condition. The outer perimeter of stabilizer 250 is illustrated as substantially flush with the outer surface of the two semi-hemispherical sections. It can be appreciated that at least a portion of the outer perimeter of the stabilizer can be recessed from an outer surface of the two semi-hemispherical sections and/or extend outwardly from the outer surface of the two semi-hemispherical sections. Connected to the stabilizer are two electrodes 260, 262. The electrodes are designed to direct current to the stabilizer. The stabilizer is formed of a material that will expand when exposed to an electrical current. The one or materials that form the stabilizer can include materials having a consistency that widely varies (e.g., about the viscosity of water (1 cps @ 70° C.) to the viscosity of a thick putty or caulk (150,000-100,000,000 cps @ 70° C.)). After stabilizer 250A has expanded to a desired shape and/or size, the expanded stabilizer can be hardened, if desired, by allowing the materials in the stabilizer to natural harden and/or to induce hardening by the use of heat, electric current, electromagnetic waves, sound waves, magnetic waves, and/or chemical reaction. Expanded stabilizer 250A is illustrated as disc shaped and extending about the central axis of spherical body 240; however, it will be appreciated that the stabilizer can have other shapes and/or be positioned in other locations on the body.

Figure 17:
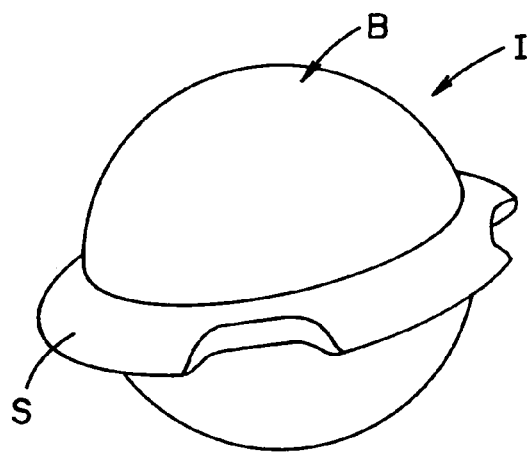
FIG. 17 is an enlarged perspective view of the prosthetic implant of the present invention illustrating a stabilizer having a variable radial width.

Referring now to FIG. 17, there is illustrated a prosthetic implant I that includes a spherical body B and an expanded stabilizer S connected to spherical body B. The stabilizer is illustrated as having various radial widths and various thicknesses at the outer edge of the stabilizer. The final configuration of the stabilizer can be selected to satisfy various needs and situations.

Figure 19A:
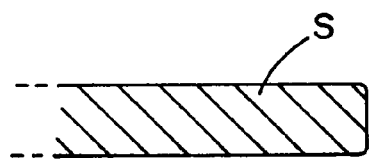
FIGS. 19A and 19B are enlarged sectional views of the end of a stabilizer.
Figure 19B:
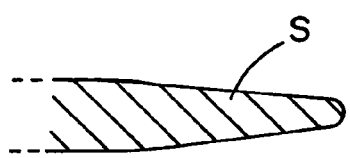
Figure 20A:
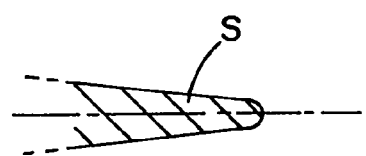
FIGS. 20A and 20B are enlarged sectional views of the end of a stabilizer illustrated relative to the central axis of the prosthetic implant.
Figure 20B:
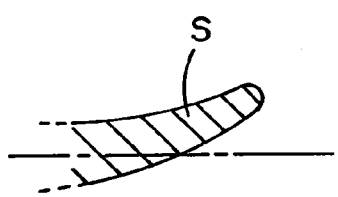

Referring now to FIGS. 19A and 19B, two enlarged cross-sections of the end portion of two stabilizers S are shown. FIG. 19A illustrates stabilizer S having a substantially uniform thickness. FIG. 19B illustrates stabilizer S having a tapered thickness. Referring now to FIGS. 20A and 20B, two enlarged cross-sections of the end portion of two stabilizers S are shown. FIG. 20A illustrates that stabilizer S expands substantially perpendicular to the outer surface of the body of the prosthetic implant. FIG. 20B illustrates that stabilizer S expands at an angle that is non-perpendicular to the outer surface of the body of the prosthetic implant. As can be appreciated, the size, shape and/or configuration of the expanded stabilizer can be customized for a particular situation.

The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

We claim:

1. A prosthetic implant to at least partially support adjoining vertebrae in a spinal column, said prosthetic implant comprising a substantially spherical or ellipsoidal body and single expandable component, said spherical or ellipsoidal body including a top portion and a bottom portion, said single expandable component at least partially positioned between said top and bottom portions, said top and bottom portions formed of a non-expandable material, said top and bottom portions designed to maintain a substantially same size and shape when said single expandable component is expanded at least a portion of said single expandable component designed to expand radially outwardly from said spherical or ellipsoidal body to at least partially form a stabilizer, said single expandable component designed to increase in surface area and have an increased sized perimeter when said single expandable component is expanded from an non-expanded state to an expanded state to at least partially form said stabilizer, said stabilizer in said expanded state having a perimeter that is greater than a perimeter of said top and bottom portions of said spherical or ellipsoidal body, said stabilizer positioned about a central axis of said substantially spherical or ellipsoidal body, said stabilizer being substantially disc shaped.

2. The prosthetic implant as defined in claim 1, wherein said top and bottom portions of said substantially spherical or ellipsoidal body are substantially non-expandable, said top and bottom portions designed to maintain a substantially same size and shape when said expandable component is expanded, said spherical or ellipsoidal body at least partially formed of one or more materials selected from the group consisting of bone, metal, ceramic material, polycarbonate, polypropylene, polyethylene, polymethylmethacrylate, polymer tilled with glass, and polymer filled with fibers.

3. The prosthetic implant as defined in claim 1, wherein said single expandable component is at least partially positioned in, on or about an outer surface of said substantially spherical or ellipsoidal body.

4. The prosthetic implant as defined in claim 1, wherein said single expandable component is at least partially expandable radially outwardly about a central axis of said substantially spherical or ellipsoidal body.

5. The prosthetic implant as defined in claim 1, wherein said single expandable component at least partially expands radially outwardly into a substantial disc shape.

6. The prosthetic implant as defined in claim 1, wherein said single expandable component includes at least one biologically active substance, said at least one biologically active substance at least one of coated on said single expandable component, contained in said single expandable component.

7. The prosthetic implant as defined in claim 1, wherein said single expandable component includes at least one biologically active substance, at least one biologically neutral substance, or combinations thereof to at least partially inhibit tissue growth, bone growth, or combinations thereof on at least a portion of said single expandable component.

8. The prosthetic implant as defined in claim 1, wherein said single expandable component includes at least one biologically active substance, at least one biologically neutral substance, or combinations thereof to at least partially promote tissue growth, bone growth, or combinations thereof on at least a portion of said single expandable component.

9. The prosthetic implant as defined in claim 1, wherein at least a portion of said single expandable component includes a substantially smooth surface.

10. The prosthetic implant as defined in claim 1, wherein at least a portion of said single expandable component includes a non-smooth surface.

11. The prosthetic implant as defined in claim 1, wherein said has a maximum radial expanded width that is up to 300% the maximum diameter of said substantially spherical or ellipsoidal body.

12. The prosthetic implant as defined in claim 1, wherein said expanded radial width of said single expandable component is substantially constant.

13. The prosthetic implant as defined in claim 12, wherein said stabilizer having a thickness that is variable, said thickness of said stabilizer adjacent to said substantially spherical or ellipsoidal body being different from said thickness of said stabilizer at a location radially spaced from said substantially spherical or ellipsoidal body, said stabilizer having a peripheral edge that is tapered.

14. The prosthetic implant as defined in claim 1, wherein said expanded radial width of said single expandable component is variable.

15. The prosthetic implant as defined in claim 1, wherein said single expandable component has a maximum expanded thickness that is less than a maximum diameter of said substantially spherical or ellipsoidal body.

16. The prosthetic implant as defined in claim 15, wherein said expanded thickness of said single expandable component is substantially constant.

17. The prosthetic implant as defined in claim 15, wherein said expanded thickness of said single expandable component is variable.

18. The prosthetic implant as defined in claim 1, wherein said single expandable component is expandable radially outwardly from said substantially spherical or ellipsoidal body along a substantially constant axis.

19. The prosthetic implant as defined in claim 1, wherein said single expandable component is expandable radially outwardly from said substantially spherical or ellipsoidal body at an angle that deviates from a substantially constant axis.

20. The prosthetic implant as defined in claim 1, wherein said single expandable component has an expanded thickness adjacent to said substantially spherical or ellipsoidal body that is different from an expanded thickness of said single expandable component at a location radially spaced from said substantially spherical or ellipsoidal body.

21. The prosthetic implant as defined in claim 20, wherein an outer perimeter of said single expandable component includes at least one tapered edge in an expanded state.

22. The prosthetic implant as defined in claim 1, wherein said single expandable component and said substantially spherical or ellipsoidal body are foiled from at least one different material.

23. The prosthetic implant as defined in claim 1, wherein said substantially spherical or ellipsoidal body includes two hemispherical or two semi-hemispherical portions, said single expandable component is portioned between said two hemispherical or two semi-hemispherical portions.

24. The prosthetic implant as defined in claim 23, wherein said single expandable component includes an elastic material at least prior to the single expandable component being expanded.

25. The prosthetic implant as defined in claim 23, wherein at least one of said two hemispherical or two semi-hemispherical portions of said substantially spherical or ellipsoidal body are formed to maintain a tension load of at least about five pounds without substantially deforming.

26. The prosthetic implant as defined in claim 1, wherein said single expandable component includes an elastic material at least prior to the single expandable component being expanded.

27. The prosthetic implant as defined in claim 26, wherein said elastic material includes an expandable pouch.

28. The prosthetic implant as defined in claim 27, wherein said expandable pouch includes at least one fluid or malleable material that is at least partially hardenable.

29. The prosthetic implant as defined in claim 27, wherein said expandable pouch is at least partially hardenable.

30. The prosthetic implant as defined in claim 26, wherein said elastic material includes an expandable wall at least partially positioned between said two hemispherical or two semi-hemispherical portions of said substantially spherical or ellipsoidal body.

31. The prosthetic implant as defined in claim 30, wherein said expandable wall at least partially retains at least one fluid or malleable material that is at least partially hardenable.

32. The prosthetic implant as defined in claim 1, wherein said expandable component includes at least one fluid or malleable material that is at least partially hardenable.

33. The prosthetic implant as defined in claim 1, wherein said substantially spherical or ellipsoidal body includes at least one cavity.

34. The prosthetic implant as defined in claim 33, wherein less than a majority of the volume of said substantially spherical or ellipsoidal body includes said at least one cavity.

35. The prosthetic implant as defined in claim 1, wherein said substantially spherical or ellipsoidal body includes an outer surface, at least a portion of said outer surface is substantially smooth.

36. The prosthetic implant as defined in claim 35, wherein said at least one opening at least partially packed with a biologically active substance, a biologically neutral substance, or combinations thereof.

37. The prosthetic implant as defined in claim 35, wherein said at least one opening including a connector that is adapted to receive an instrument to guide said prosthetic implant between adjoining vertebrae in a spinal column, to receive a component of a stabilization system, or combinations thereof.

38. The prosthetic implant as defined in claim 35, including a cap to at least partially cover or seal said at least one opening.

39. The prosthetic implant as defined in claim wherein said substantially spherical or ellipsoidal body includes an outer surface, at least a portion of said outer surface is substantially non-smooth.

40. The prosthetic implant as defined in claim 1, wherein said substantially spherical or ellipsoidal body includes an outer surface, said outer surface at least partially coated with a biologically active substance, a biologically neutral substance, or combinations thereof.

41. The prosthetic implant as defined in claim 1, wherein said substantially spherical or ellipsoidal body includes at least one opening.

42. The prosthetic implant as defined in claim 41, wherein said mechanical compression arrangement includes a threaded member.

43. The prosthetic implant as defined in claim 1, wherein said substantially spherical or ellipsoidal body includes a mechanical compression arrangement that is adapted to at least partially compress together at least two portions of said spherical or ellipsoidal body.

44. The prosthetic implant as defined in claim 1, wherein said substantially spherical or ellipsoidal body includes a memory material.

45. The prosthetic implant as defined in claim 1, wherein said single expandable component includes a memory material.

46. The prosthetic implant as defined in claim 1, wherein said substantially spherical or ellipsoidal body includes at least one electrical connection.

47. The prosthetic implant as defined in claim), wherein said single expandable component includes at least one electrical connection.

48. The prosthetic implant as defined in claim 1, wherein said substantially spherical or ellipsoidal body includes at least one pressure sensor.

49. The prosthetic implant as defined in claim 1, wherein said expandable component includes at least one pressure sensor.

50. The prosthetic implant as defined in claim 1, wherein said single expandable component in an expanded state expanding from an outer surface of said spherical or ellipsoidal body a distance of 0.01%-300% a diameter of said spherical or ellipsoidal body.

51. The prosthetic implant as defined in claim 1, wherein said stabilizer having a thickness that is variable, said thickness of said stabilizer adjacent to said substantially spherical or ellipsoidal body being different from said thickness of said stabilizer at a location radially spaced from said substantially spherical or ellipsoidal body, said stabilizer having a peripheral edge that is tapered.

52. A method of expanding an expandable stabilizer of a prosthetic implant comprising:
   a. selecting a prosthetic implant having a substantially spherical or ellipsoidal body and at least one expandable component, said spherical or ellipsoidal body including a top portion and a bottom portion, said expandable component at least partially positioned between said top and bottom portions; and,
   b. applying pressure to at least a portion of said at least one expandable component until said at least one expandable component at least partially radially expands, said at least one expandable component designed to increase in surface area and having an increased sized perimeter when said at least one expandable component is expanded from an non-expanded state to an expanded state, said expandable component in said expanded state having an increased perimeter that is greater than a perimeter of said top and bottom portions of said spherical or ellipsoidal body.

53. The method as defined in claim 52, wherein said top and bottom portions maintain a substantially same size and shape prior to and after said expandable component is expanded.

54. A method of expanding an expandable stabilizer of a prosthetic implant comprising:
 a. selecting a prosthetic implant having a substantially spherical or ellipsoidal body and at least one expandable component, said spherical or ellipsoidal body including a top portion and a bottom portion, said expandable component at least partially positioned between said top and bottom portions; and,
 b. causing at least one material of said at least one expandable component to chemically react and form an expanded composition until said at least one expandable component at least partially expands, said at least one expandable component designed to increase in surface area and having an increased sized perimeter when said at least one expandable component is expanded from an non-expanded state to an expanded state, said expandable component in said expanded state having am increased perimeter that is greater than a perimeter of said top and bottom portions of said spherical or ellipsoidal body.

55. The method as defined in claim 54, wherein said top and bottom portions maintain a substantially same size and shape prior to and after said expandable component is expanded.

* * * * *